United States Patent [19]

Owen et al.

[11] Patent Number: 5,633,226

[45] Date of Patent: *May 27, 1997

[54] CONVERTIBLE MICROEMULSION FORMULATIONS

[75] Inventors: Albert J. Owen, West Chester, Pa.; Seang H. Yiv, Wilmington, Del.

[73] Assignee: LDS Technologies, Inc., Boothwyn, Pa.

[*] Notice: The term of this patent shall not extend beyond the expiration date of Pat. No. 5,444,041.

[21] Appl. No.: 425,787

[22] Filed: Apr. 20, 1995

Related U.S. Application Data

[63] Continuation of Ser. No. 885,202, May 20, 1992, Pat. No. 5,444,041, which is a continuation-in-part of Ser. No. 841,931, Feb. 25, 1992, abandoned, which is a continuation-in-part of Ser. No. 837,347, Feb. 14, 1992, abandoned, which is a continuation-in-part of Ser. No. 687,691, Apr. 19, 1991, abandoned.

[30] Foreign Application Priority Data

Apr. 15, 1992 [WO] WIPO ............... PCT/US92/03086

[51] Int. Cl.$^6$ .......................... A61K 9/107; A61K 38/00; A61K 38/16; A61K 39/00
[52] U.S. Cl. .......................... 514/2; 424/400; 424/193.1; 514/784; 514/937
[58] Field of Search .......................... 514/2, 3, 12, 937, 514/938, 940, 784; 424/94.3, 193.1, 196.11, 197.11, 400, 463

[56] References Cited

U.S. PATENT DOCUMENTS

| | | | |
|---|---|---|---|
| 3,083,142 | 3/1963 | Howell et al. | 424/92 |
| 3,100,178 | 8/1963 | McLean et al. | 424/89 |
| 3,149,036 | 9/1964 | Woodhour et al. | 424/89 |

(List continued on next page.)

FOREIGN PATENT DOCUMENTS

| | | |
|---|---|---|
| 0135171 | 3/1985 | European Pat. Off. . |
| 0274870 | 12/1987 | European Pat. Off. . |
| 0278660 | 2/1988 | European Pat. Off. . |
| 0257368 | 3/1988 | European Pat. Off. . |
| 0429248 | 11/1990 | European Pat. Off. . |
| 0314689 | 4/1992 | European Pat. Off. . |
| 3919982 | 6/1989 | Germany . |
| 53-50316 | 5/1978 | Japan . |
| 61-185332 | 8/1986 | Japan . |
| 1171125 | 11/1969 | United Kingdom . |
| 2098865 | 12/1982 | United Kingdom . |
| WO86/02264 | 10/1985 | WIPO . |
| WO88/00059 | 1/1988 | WIPO . |
| WO93/02664 | 2/1993 | WIPO . |
| WO93/02665 | 2/1993 | WIPO . |
| WO93/06921 | 4/1993 | WIPO . |
| WO94/08603 | 4/1994 | WIPO . |
| WO94/08605 | 4/1994 | WIPO . |
| WO94/08610 | 4/1994 | WIPO . |

OTHER PUBLICATIONS

Charman, S. et al., "Self-Emulsifying Drug Delivery Systems: Formulaiton and Biopharmaceutic Evaluation of an Investigational Lipophilic Compound", *Pharmaceutical Research* 1992, 9(1), 87–93.

Engstrom, L. "Aggregation and Structural Changes in the L2-Phase in the System Water/Soybean Oil/Sunflower Oil Monoglycerides", *J. Dispersion Science and Technology* 1990, 11(5), 479–489.

(List continued on next page.)

*Primary Examiner*—Jeffrey E. Russel
*Attorney, Agent, or Firm*—Woodcock Washburn Kurtz Mackiewicz & Norris

[57] ABSTRACT

There is provided a water-in-oil (w/o) microemulsion which readily converts to an oil-in-water (o/w) emulsion by the addition of aqueous fluid to the w/o microemulsion, whereby any water-soluble biologically-active material in the aqueous phase is released for absorption by the body. The w/o microemulsion is particularly useful for storing proteins and the like for long periods of time at room temperature and above until they are ready for use, at which time the addition of aqueous fluid converts the microemulsion to an o/w emulsion and releases the protein.

20 Claims, 5 Drawing Sheets

OIL: CAPTEX 200
SURFACTANT: (CAPMUL:MYVEROL:CREMOPHOR:)(45.5:5.2:49.2)
AQUEOUS: 0.9% NaCl

□ MAX AQ%(w/w)    ○ MAX.MIN AQ%(w/w)
▲ MIN AQ%(w/w)    × MIN.MIN AQ%(w/w)

U.S. PATENT DOCUMENTS

| | | | |
|---|---|---|---|
| 3,438,782 | 4/1969 | Elenbogen et al. | 426/72 |
| 3,492,399 | 1/1970 | Prigal | 424/91 |
| 3,776,857 | 12/1973 | Lindner | 252/308 |
| 3,983,228 | 9/1976 | Woodhour et al. | 424/89 |
| 4,094,971 | 6/1978 | Chedid et al. | 424/92 |
| 4,104,403 | 8/1978 | Barker et al. | 424/61 |
| 4,122,158 | 10/1978 | Schmitt | 424/94.61 |
| 4,183,918 | 1/1980 | Asher et al. | 424/600 |
| 4,241,051 | 12/1980 | Christie et al. | 530/307 |
| 4,395,394 | 7/1983 | Wolff, III et al. | 424/88 |
| 4,460,692 | 7/1984 | Tellier et al. | 435/248 |
| 4,481,188 | 11/1984 | Apontowell et al. | 424/89 |
| 4,650,677 | 3/1987 | Roerink | 424/89 |
| 4,690,774 | 9/1987 | Vishnupad et al. | 252/309 |
| 4,692,433 | 9/1987 | Hostetler et al. | 514/12 |
| 4,711,902 | 12/1987 | Serno | 514/356 |
| 4,719,239 | 1/1988 | Muller et al. | 514/785 |
| 4,720,353 | 1/1988 | Bell | 252/309 |
| 4,731,384 | 3/1988 | Dell et al. | 514/658 |
| 4,781,914 | 11/1988 | Deckner | 424/59 |
| 4,797,273 | 1/1989 | Linn et al. | 424/59 |
| 4,803,070 | 2/1989 | Cantrell et al. | 424/92 |
| 4,806,350 | 2/1989 | Gerber | 424/92 |
| 4,806,352 | 2/1989 | Cantrell | 424/92 |
| 4,914,084 | 4/1990 | Ecanow | 514/6 |
| 4,931,210 | 6/1990 | Takahashi et al. | 514/558 |
| 4,963,367 | 10/1990 | Ecanow | 424/485 |
| 4,980,084 | 12/1990 | Vishnupad et al. | 514/942 |
| 5,002,771 | 3/1991 | Purkaystha et al. | 424/433 |
| 5,026,825 | 6/1991 | Grebow et al. | 530/307 |
| 5,036,045 | 7/1991 | Thorner | 514/12 |
| 5,036,108 | 7/1991 | Asahi et al. | 514/937 |
| 5,037,653 | 8/1991 | Dawson | 424/405 |
| 5,045,337 | 9/1991 | El Nokaly et al. | 426/602 |
| 5,064,653 | 11/1991 | Session et al. | 424/404 |
| 5,084,289 | 1/1992 | Shin et al. | 424/439 |
| 5,110,606 | 5/1992 | Geyer et al. | 424/489 |
| 5,162,378 | 11/1992 | Guthauser | 514/785 |
| 5,206,219 | 4/1993 | Desai | 514/3 |
| 5,444,041 | 8/1995 | Owen et al. | 514/2 |

OTHER PUBLICATIONS

Engstrom, S. et al., "Enzyme Stabilization in Composite Cubic Phases", *Annals New York Academy of Sciences* 1990, 613, 429–30.

Engstroem, S., "Cubic Phases as Drug Delivery Systems", *Am. Chem. Soc., Div. Polym. Chem.* 1990, 31(2), 157–158.

Fletcher, P. and Parrott, "The Partitioning of Proteins between Water–in–oil Microemulsions and Conjugate Aqueous Phases", *J. Chem. Soc., Faraday Trans. 1,* 1988, 84(4), 1131–1144.

Fiedler, H.P., "Index of Auxiliary Substances", *Pharm. Ind.* 1989, 12, 1446–1449.

Friberg, S. and Mandell, "Phase Equilibria and Their Influence on the Properties of Emulsions", *J. of the Am. Oil Chemists' Society* 1970, 47, 149–152.

Ganguly, R. and Waldman, "Active and Passive Immunization", in Fundamentals of Immunology and Allergy Lockey and Bukantz, ed., W.B. Saunders Company, Philadelphia, 1987, pp. 243–259.

Gulik–Krzywicki, T. and Larsson, "An Electron Microscopy Study of the L2–Phase (Microemulsion) in a Ternary System: Triglyceride/Monoglyceride/Water", *Chemistry and Physics of Lipids* 1984, 35, 127–132.

Kale, N. and Allen, "Studies on Microemulsions Using Brij 96 as Surfactant and Glycerin, Ethylene Glycol and Propylene Glycol as Cosurfactants", *Int. J. of Pharmaceutics* 1989, 57, 87–93.

Kemken, J. et al., "Influence of Supersaturation on the Pharmacodynamic Effect of Bupranolol After Dermal Administration Using Microemulsions as Vehicle", *Pharmaceutical Research* 1992, 9(4), 554–558.

"Kirk–Othmer Encyclopedia of Chemical Technology", 3rd Ed, vol. 8, pp. 908, 913–918, 929, John Wiley & Sons, New York, 1979.

Larsson, K., "Emulsions of Reversed Micellar Phases and Aqueous Dispersions of Cubic Phases of Lipids", *Am. Chem. Soc.* 1991, 45–50.

Luisi, P.L. et al., "Reverse Micelles as Hosts for Proteins and Small Molecules", *Biochim. Biophys. Acta* 1988, 947, 209–246.

Muller, B.W. and Kleinebudde, "Investigations of So–Called Microemulsion Systems. Part 1: Investigations of Drug–Free Systems", *Pharm. Ind.* 1988, 50(3), 370–375.

Muller, B.W. and Kleinebudde, "Investigations of So–Called Microemulsions. Part 2: Investigations of Drug–Containing Systems", *Pharm. Ind.* 1988, 50(11), 1301–1306.

Overkamp, D. et al., "Production of Polyclonal Antibodies in Ascitic Fluid of Mice: Technique and Applications", *J. of Immunoassay* 1988, 9(1), 51–68.

Pilman, E. et al., "Inverse Micellar Phases in Ternary Systems of Polar Lipids/Fat/Water and Protein Emulsification of Such Phases to Water/Oil/Water–Microemulsion–Emulsions", *J. Dispersion Science and Technology* 1980, 1(3), 267–281.

Ritschel, W.A., "Microemulsion for Improved Peptide Absorption from the Gastrointestinal Tract", *Meth. Fund. Exp. Clin. Pharmacol.* 1991, pp. 205–220.

Rizzo, V., "Hydrophilic Molecules Solubilized in Water–in–Oil Microemulsions: Distribution of Species in a Chemical Equilibrium", *J. of Colloid and Interface Science* 1986, 110(1), 110–113.

Thompson, K. and Gierasch, "Conformation of a Peptide Solubilizate in a Reversed Micelle Water Pool", *J. Am. Chem. Soc.* 1984, 106, 3648–3652.

Pouton, C.W., "A Study of Self–Emulsifying Oil/Surfactant Mixtures", Dept. of Pharmacy, Chelsea College, University of London, Jan. 1982, pp. 1–252.

Wakerly, M.G., "Self–Emulsifying Drug Delivery Systems Based on Nonionic Surfactant–Oil Mixtures", University of Bath, 1989.

Ser. No. 07/962,956 filed Oct. 16, 1992 by Constantinides.

Ser. No. 07/962,957 filed Oct. 16, 1992 by Constantinides.

Langmuir, vol. 4, issued 1988, Gestblom et al, "Dielectric Properties of Some Microemulsions . . . ", pp. 360–364.

J. Phys. Chem. vol. 85, issued 1981, Fabre et al, "Aggregation In Three–Component Surfactant Systems . . . ", pp. 3493–3501.

Budavari et al, The Merck Index, published 1989 by Merck & Co. Inc. (Rahway), p. 1213.

OIL: CAPTEX 200
SURFACTANT: (CAPMUL: MYVEROL: CREMOPHOR:)(45.5:5.2:49.2)
AQUEOUS: 0.9% NaCl

- □ MAX AQ%(w/w)
- ▲ MIN AQ%(w/w)
- ○ MAX.MIN AQ%(w/w)
- × MIN.MIN AQ%(w/w)

OIL: CAPTEX 200
SURFACTANT: (CAPMUL; CENTROPHASE; TWEEN)(46:10.6:43.4)
AQUEOUS: 0.9% NaCl

- MIN Aq %(w/w)
- MAX AQ %(w/w)

OIL: CAPTEX 200
SURFACTANT: (CAPMUL: CENTROPHASE: CREMOPHOR)(31.5:6:62.5)
AQUEOUS: 0.9% NaCl

MIN Aq % (w/w)

MAX AQ % (w/w)

OIL: WITEPSOL H-15
SURFACTANT: (CAPMUL: MYVEROL: TWEEN)(15.4:8.5:76.0)
AQUEOUS: 20% SORBITOL IN 0.9% NaCl(w/w)

- MIN Aq%(w/w)
- MAX AQ%(w/w)

SEQUENCE LISTING ( 1 ) GENERAL INFORMATION:

( i i i ) NUMBER OF SEQUENCES: 2

( 2 ) INFORMATION FOR SEQ ID NO:1:

```
       ( i ) SEQUENCE CHARACTERISTICS:
               ( A ) LENGTH: 5 amino acids
               ( B ) TYPE: amino acid
               ( D ) TOPOLOGY: circular ( i i ) MOLECULE TYPE: peptide ( i x ) FEATURE:
               ( A ) NAME/KEY: Modified-site
               ( B ) LOCATION: 1
               ( D ) OTHER INFORMATION: /note=N- acetyl-Cys ( i x ) FEATURE:
               ( A ) NAME/KEY: Disulfide-bond
               ( B ) LOCATION: 5
               ( D ) OTHER INFORMATION: /note=Penicillamine amide ( i x ) FEATURE:
               ( A ) NAME/KEY: Disulfide-bond
               ( B ) LOCATION: 1..5

( i x ) FEATURE:
               ( A ) NAME/KEY: Modified-site
               ( B ) LOCATION: 2
               ( D ) OTHER INFORMATION: /note=alpha-N-methyl-Arg ( x i ) SEQUENCE DESCRIPTION: SEQ ID NO:1:
               Cys  Arg  Gly  Asp  Xaa
               1                   5

( 2 ) INFORMATION FOR SEQ ID NO:2:

( i ) SEQUENCE CHARACTERISTICS:
               ( A ) LENGTH: 7 amino acids
               ( B ) TYPE: amino acid
               ( D ) TOPOLOGY: circular ( i i ) MOLECULE TYPE: peptide ( i x ) FEATURE:
               ( A ) NAME/KEY: Modified-site
               ( B ) LOCATION: 1
               ( D ) OTHER INFORMATION: /note=N- acetyl-Cys ( i x ) FEATURE:
               ( A ) NAME/KEY: Disulfide-bond
               ( B ) LOCATION: 1..7

( i x ) FEATURE:
               ( A ) NAME/KEY: Modified-Site
               ( B ) LOCATION: 3
               ( D ) OTHER INFORMATION:
                     / note="4,4'-Dimethylthiazolidine-5-carboxycylic acid"

( i x ) FEATURE:
               ( A ) NAME/KEY: Modified-Site
               ( B ) LOCATION: 4
               ( D ) OTHER INFORMATION:
                     / note="para-aminomethylphenylalanine"

( x i ) SEQUENCE DESCRIPTION: SEQ ID NO:2:
               Cys  Asn  Xaa  Xaa  Gly  Asp  Cys
               1                   5
```

CONVERTIBLE MICROEMULSION FORMULATIONS

FIELD OF THE INVENTION

This is a continuation of application Ser. No. 885,202 filed May 20, 1992, now U.S. Pat. No. 5,444,041, which is related to PCT application PCT US92 03086 filed Apr. 15, 1992, and is also a continuation-in-part of application Ser. No. 841,931, filed Feb. 25, 1992, now abandoned, which is a continuation-in-part of application Ser. No. 837,347, filed Feb. 14, 1992, now abandoned, which in turn is a continuation-in-part of application Ser. No. 687,691, filed Apr. 19, 1991, now abandoned.

This invention relates to microemulsions, and methods of making and using the same. More particularly, it relates to certain unique microemulsion formulations which are phase reversible (i.e., "convertible" as defined below), methods for making and storing them, and their use in administering drugs, proteins, and like biologically-active materials, including therapeutically-active ones.

As used herein, the microemulsions of this invention are self-emulsifying stable dispersions of oil and water, stabilized by interfacial films of surface-active molecules. These microemulsions are also characterized by their small average particle sizes, generally less than about 0.1 micron, by their wide range of temperature stability, typically from about 5° C. to 50° C., and they appear to be thermodynamically-stable, i.e., stable indefinitely over this range. They are also relatively insensitive to the pH or ionic strength of the aqueous internal phase.

These microemulsions are further characterized in that they form spontaneously without the need of high shear equipment, as distinct from conventional emulsions (macroemulsions) which must be prepared by the input of significant amounts of energy, and which are thus subject to extremes of temperature, pressure, and shear, resulting in damage to the contents of the emulsion. For further discussion of these systems, see "Microemulsions," M. Kahlweit, *Science*, 240:617–621 (1988).

By the term "convertible" or "phase reversible", as used herein to describe the microemulsions of this invention, is meant a microemulsion formulation capable of being changed from a water-in-oil (w/o) system to an oil-in-water (o/w) system by the addition of water to the former, as described in further detail below.

Also, "conversion," as used herein, is intended to define in particular the reversal of a w/o emulsion to form an o/w emulsion, as distinct from the term "inversion", as used in the art, which describes principally the change of a w/o emulsion to a water-in-oil-in-water (w/o/w) formulation.

BACKGROUND OF THE INVENTION

The preparation and use of microemulsions in the formulation of drugs, proteins, and the like are known in the art. See, for example, U.S. Pat. No. 3,989,843, which discloses the application of microemulsions to medical formulations. Also, in *Eur. J. Biochem.*, Samama et al., 163 (3):609–617 (Mar. 16, 1987) describe liver alcohol dehydrogenase in ionic w/o microemulsions, while Lee et al. describe the extraction of epoxide cyclase, using various ionic microemulsions, in *FEBS Lett.*, 244 (2):347–50 (Feb. 27, 1989). In each case, however, there is no teaching or suggestion that these microemulsions are phase reversible.

U.S. Pat. Nos. 4,931,210; 4,857,506; 4,714,566; and 4,590,086, on the other hand, disclose methods of preparing water-in-oil emulsions which are then inverted to form well-known water-in-oil-in-water phase (w/o/w) emulsions. These complex preparations, however, are macroemulsion formulations requiring high shear energy to prepare, and the resulting product is a w/o/w emulsion which actually comprises a w/o emulsion mixed into an aqueous phase in such a way that the first internal aqueous phase does not mix with the second continuous aqueous phase.

Emulsion systems for delivery of lipophilic agents via oral, parenteral, or local cutaneous administration and for transdermal delivery of the polypeptide hirudin are disclosed in U.S. Pat. No. 4,719,239 to Muller et al. Microemulsion systems containing drugs having a good hydrophilic/lipophilic balance for transdermal delivery are disclosed in GB Application 2,098,865. These references fail to disclose the use of a water-in-oil microemulsion for the mucosal delivery of a water-soluble active agent, such as proteins and peptides.

Emulsion systems have also been used as vaccine adjuvant systems, particularly water-in-oil emulsions. The strength of the immune response and the speed with which it is evoked can be modified by the nature of the liquid matrix of the vaccine. One widely-used example of such a system is Freund's adjuvant, which consists of paraffin oil and a surfactant, mannide mono-oleate. These adjuvant emulsions, due to their thermodynamic instability, must be emulsified with a solution containing the immunogen just prior to injection of the vaccine. In addition, the paraffin oil in the adjuvant can lead to inflammation of the injection site and formation of granulomas. These two effects are greatly enhanced if immune stimulators are also employed. The oil and immune stimulators are helpful, however, in that they stimulate immune response by enhancing the activity of macrophages. These macrophages engulf the emulsion droplets and process the immunogen at the site of the injection. It would, therefore, be beneficial to be able to produce a vaccine adjuvant system which has a prolonged stability and thus, a prolonged shelf life in its prepared microemulsion state, and which can be formulated with a biodegradable oil which would not stimulate granuloma production.

There is a continuing need for new and improved delivery systems for biologically active materials. Many of the therapeutic agents emerging from the biotechnology revolution, as well as some older drugs such as insulin and calcitonin, consist of large-molecule proteins. These drugs must now be injected into the patient because they are unable to survive the digestive process and do not readily pass through the mucosal lining of the gastrointestinal tract and enter the bloodstream. A new drug delivery system that would enable proteins to enter the bloodstream through, for example, the lining of the digestive system would be of great benefit.

Improved drug delivery systems could also provide much improved convenience for patients. For example, calcitonin is a generic peptide hormone used for treatment of osteoporosis and other diseases involving bone loss. Osteoporosis affects 24 million Americans, including ⅔ of the women past menopause. Currently, most calcitonin is delivered by injection. Calcitonin treatment for osteoporosis requires long-term administration with low but frequent doses of the drug. An oral or suppository formulation of calcitonin would offer great advantages to patients underoing such treatments.

SUMMARY OF THE INVENTION

In accordance with the present invention, there is now provided a composition comprising a highly stable waterin-oil microemulsion containing biologically, including therapeutically, active water-soluble materials in its internal aqueous phase, which water-soluble materials are controllably releasable when needed just prior to administration by the ready conversion of the microemulsion into an oil-in-water emulsion by the addition of water to form a continuous aqueous phase.

The invention also relates to the preparation of such microemulsions and their use in the administration of biologically and therapeutically active water-soluble materials.

One aspect of the invention is the storage or maintenance of materials, such as proteins and peptides, in a solubilized state at temperatures or conditions at which they would otherwise be unstable. For example, it has been found that some proteins can be stored dissolved in the aqueous phase of the w/o microemulsions at temperatures at which the protein would be unstable if stored merely as an aqueous solution. Such proteins may be stored in a w/o microemulsion of this invention until ready to be used, at which time water is then added until an o/w emulsion has formed, which emulsion is then administered orally or by injection. Also, the stored w/o microemulsion can be administered to the body wherein it is converted to an o/w emulsion by the addition of bodily fluids. In this manner, storage problems are lessened or eliminated.

Typical of the storage times for drugs, proteins, and the like, which may be achieved with the compositions of this invention, are times anywhere from about 1 to 48 hours, preferably 16–24 hours up to several, i.e., 3–12, weeks or months, at temperatures of from about room temperature, i.e., about 20° C., up to the temperature where the microemulsion breaks, generally in the range of about 50°–70° C., preferably below about 40° C. Temperatures below room temperature can, of course, be used.

In a further aspect of this invention, it has been found that, unexpectedly, if a w/o microemulsion of this invention containing, for example, a water-soluble drug in the internal aqueous phase, is administered directly to the body of animals, including humans, the body fluids themselves are sufficient to convert the w/o microemulsion to an o/w emulsion, thereby slowly releasing the drug in situ. This is particularly advantageous over pre-conversion with water in that because body fluids are employed, the total volume of liquid administered is smaller. This method is particularly useful in administration into the colon or intestines of such drugs as peptides, proteins, or other molecules with bonds that are readily attacked by enzymes, where the oil protects the drug in the intestines until it is slowly released as the body fluids convert the emulsion. In the case of calcitonin, for example, if it is administered into the colon as just an aqueous solution, colon enzymes destroy the drug before it is absorbed, whereas with the microemulsion formulations of this invention, the calcitonin is protected from the enzymes until it is slowly released by hydration within the body.

In one particular embodiment of the present invention the w/o microemulsion system is formulated such that, upon conversion with additional water, an o/w microemulsion is formed. Such a system is advantageous in that the converted system has a small particle size. In another embodiment of the present invention, the microemulsion system is formulated as a solid at room temperature which has surprisingly been found to enhance drug uptake and activity for gastrointestinal delivery.

A particular embodiment of the present invention is the use of a w/o microemulsion as a vaccine adjuvant system. The immunogen is carried in the aqueous phase of the microemulsion adjuvant system, which when introduced into the body and contacted with aqueous bodily fluids, undergoes conversion to form an oil-in-water emulsion.

"Administration to the body", as used herein for systems that convert to macroemulsions, includes any non-intravenous method such as intramuscular, subcutaneous, oral, rectal, or peritoneal means. More specifically, the w/o microemulsion is administered parenterally, enterally, or via any other mucous membrane. Systems that convert to microemulsions can also be administered intravenously and intraarterially.

In yet another embodiment of this invention, it has been determined that these w/o microemulsions may also be used to formulate topical salves which are highly advantageous in that they remain moist on the skin for long periods of time without drying and crumbling.

DESCRIPTION OF THE INVENTION

Figure 1:
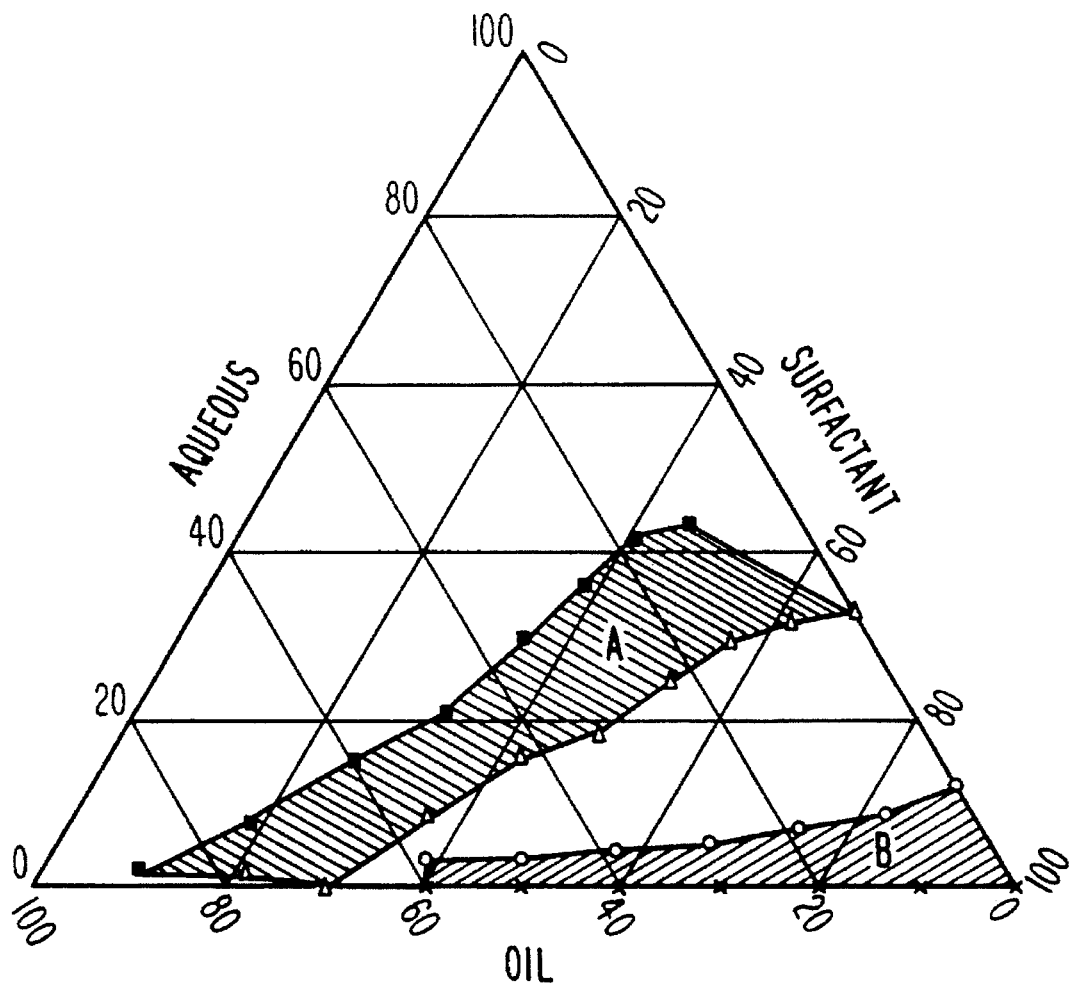
FIG. 1 is a phase diagram of an embodiment of the present invention depicting the water-in-oil microemulsion region wherein the oil is Captex 200, the aqueous phase is a 0.9% wt. NaCl aqueous solution, and the surfactant mixture is Capmul MCM:Myverol 18–92:Cremophor EL.

The biologically active material composition of this invention comprises, at a minimum, (1) an aqueous phase; (2) a pharmaceutically-acceptable oil, or mixtures thereof; (3) an oil-dispersible surfactant, or mixtures thereof; and (4) a water-soluble biologically active material or combination of materials. In addition, there may optionally be included such other adjuvants as stabilizers, coloring agents, oil soluble drugs and the like. Each of these components and adjuvants must be suitable for use in the subject and will usually be food grade and/or pharmaceutically-acceptable materials. Any drugs will be present in therapeutically-effective amounts. The compositions of the present invention are biologically compatible water-in-oil (w/o) microemulsions. These compositions are biologically compatible in that they are non-toxic and contain biodegradable or non-absorbable materials. By non-toxic it is meant non-toxic dependent upon the route of administration to a subject, in that the toxicity of one route may not be equivalent to that of another route.

The microemulsions of the present invention are created by the interplay between the surfactant or mixture of surfactants and the oil and aqueous phases. The surfactant or mixture of surfactants preferably have a hydrophilic-lipophilic balance (HLB) within a specified range. By "hydrophilic-lipophilic balance" is meant an empirical quantity, on an arbitrary scale, which is a measure of the polarity of a surfactant or mixture of surfactants. See P. Becher et al., "*Nonionic Surfactant, Physical Chemistry,*" Marcel Dekker, NY (1987), pages 439–456. It is a widely known and used term. The w/o microemulsions can be solids including semi-solids, gels, or liquids at room temperature.

More particularly, the amount of the components should be such that the biologically-active material comprises from $10^{-9}$ to 100 weight/volume %, based on the volume of the aqueous phase. Generally, in the microemulsion system, the aqueous phase ranges up to about 60 volume percent; the oil content ranges from about 5 to about 99, preferably from about 10 to about 99 volume percent; the surfactant content ranges from about 1 to about 70 volume percent.

The water content in the w/o microemulsions is up to about 20 volume percent, preferably up to about 30 volume percent, most preferably up to about 40 volume percent, and in some cases as high as 60 volume percent of the microemulsion. In a preferred high aqueous phase content w/o microemulsion system, the aqueous phase content ranges from about 20 to about 60 volume percent, preferably from about 30 to about 60, most preferably about 40–55%; the oil content ranges from about 5 to about 50 volume percent, preferably from about 5 to about 40, most preferably about 5–15%; the surfactant content ranges from about 5 to about 75 volume percent, preferably from about 20 to about 65, most preferably about 40–50%. In a preferred low aqueous phase content w/o microemulsion system, the aqueous phase should comprise no more than about 20%, preferably the aqueous phase content ranges from about 0.1 to about 20 volume percent, most preferably about 0.1–15%; the oil content ranges from about 30 to about 99 volume percent, preferably about 50–90%; the surfactant content ranges from about 1 to about 70 volume percent, preferably about 2–50%. When the aqueous phase of the w/o microemulsion is below about 20% volume, it is preferred to have a ratio of oil phase to low HLB surfactant, HLB below about 8, preferably below about 5, of at least 6:1, and preferably at least about 10:1. The water component of the aqueous phase can be partially or fully replaced by the incorporation of another polar, biologically compatible solvent such as polyhydrolic alcohols having at least 2 hydroxyl groups, glycerol, propylene glycol, and mixtures thereof, however it is preferred to have the aqueous phase consist of at least 30%, and most preferably 50% water. Thus, the term "aqueous phase" as used herein is intended to encompass a phase comprising water, such polar solvents, and mixtures thereof. The aqueous phase may comprise, in addition to water (or other polar solvent) and active material, such other adjuvants such as, but not limited to, stabilizers, coloring agents, modifiers, and the like, or salts (e.g., when saline is used).

The formulation of a microemulsion having a high aqueous phase content is preferred in those situations where the biologically-active material has a relatively low solubility in water or where a relatively high quantity of the biologically-active material is desired in the microemulsion system.

Adjuvants, such as preservatives, coloring agents, flavors or oil-soluble drugs, e.g., steroids, if any, should be included only in those amounts which will not adversely affect the novel properties of the microemulsion, generally in amounts of from about 0 to 20% by volume, based on the total volume of the composition.

In the following description it will be understood that the nature of the oils and surfactants is not critical beyond those particular qualifications set forth below, and may generally be any such known materials conventionally employed and which are accepted in the food and pharmaceutical industry.

The oil, or mixtures thereof, may be liquid at room temperature, although in some cases, mild heating of a solid oil to form a liquid is acceptable. If injection is the preferred route of administration, the oil should be liquid at room temperature. Heating of an oil that is solid at room temperature is desirable for formulations intended as suppositories, creams, salves, and in some cases as oral capsules. Illustrations of suitable oils for purposes of this invention include triesters of glycerol having from about 9 to 83, preferably 20–60, carbon atoms, and diesters of propylene glycol having from about 7 to 55, preferably 15–40 carbon atoms, most preferably propylene glycol esters of capric and caprlic acids having from 19 to 23 carbon atoms. The triglycerides are further defined as short chain triglycerides having 9–15 carbon atoms, medium chain triglycerides having 21–45 carbon atoms, and long chain triglycerides having above 45 carbon atoms. Short chain and medium chain, and preferably short chain, triglycerides are preferred for liquid w/o microemulsion systems. The diesters of propylene glycols are further defined as short chain having from 7–11 carbon atoms, medium chain having from 15–31 carbon atoms, and long chain having above 31 carbon atoms. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Diesters of propylene glycols include propylene glycol esters of capric and caprylic acids, such as Captex 200® (Karlshamns Lipid Specialities, Columbus, Ohio) and other ester groups as described above for glycerol.

As shown in the data below, it has been found in another embodiment that, surprisingly, when a mixture of an oil and mono and diglyceride surfactants, particularly Captex 200® and Capmul MCM®, manufactured by Karlshamns Lipid Specialities of Columbus, Ohio, as defined below, are used together, there is a significant enhancement in activity of the active ingredient. Therefore, depending upon the nature of the drug, mixtures of oils and mono and diglycerides may be preferred.

The surfactant, or more preferably, the mixture of surfactants, should be chosen from those having a resulting HLB value in the range of from about 7 to 14, more preferably 8 to 13. When a mixture of surfactants is employed, while some of the components may have a value outside the desired range, e.g., below about 5, it will be understood that by mixing in surfactants with HLB's greater than, e.g., about 9, the resulting combined HLB value will be in the range of 7 to 14. Also, when a mixture is employed, it is desirable that at least one of these surfactants have a molecular weight of at least about 500, although this weight is not critical. It has been found that although some protein and peptide delivery systems require the presence of certain surfactants, such as sterols or lecithin, the present w/o microemulsion systems do not require any particular surfactant or surfactant mixture, and can be essentially free, that is containing less than about 0.05% wt. in the w/o microemulsion, of any of the listed surfactants. However, to promote bioavailability of the active agent, certain surfactants are preferred.

A mixture of surfactants is preferred when the w/o microemulsion has an aqueous phase content of greater than about 20% by volume. The mixture includes a high HLB surfactant or mixtures of high HLB surfactants, having a HLB value of greater than 9 and preferably at least one surfactant having a HLB value greater than about 12. In some embodiments having a relatively high aqueous phase content above about 40% by volume, it is preferred to have at least one surfactant with a HLB greater than about 15, and a low HLB surfactant having a HLB value below about 5, which together have an average HLB value of from about 7 to 14. Further, the surfactant should desirably be highly oil-soluble or oil-dispersible, and the ready addition of the surfactant to the oil thus makes for easier processing.

Surfactants which may be employed in our compositions include both ionic agents, i.e., cationic, anionic or zwitterionic, and non-ionic agents, or mixtures thereof. Examples of cationic surfactants include cetyldimethylethylammonium bromide, cetylpyridinium chloride and other salts of these surfactants.

Examples of anionic surfactants include $C_{8-32}$ fatty acids and salts thereof; cholic acid and derivatives thereof such as deoxycholate, and its salts, ursodeoxycholic acid, and taurocholic acid; $C_{8-56}$ diesters of tartaric acid; phospholipids such as phosphatidic acid and phosphatidyl serine; $C_{5-29}$ monoesters of lactic acid; $C_{8-20}$ sulfonates, including alkyl-, olefin-, and alkylaryl derivatives; tridecyl- and dodecylbenzene sulfonic acids; and $C_{5-33}$ sarcosine and betaine derivatives.

Zwitterionics include such phospholipids as lecithin, phosphatidylethanolamine, and sphingomyelins.

Among the non-ionic surfactants which may be employed are ethoxylated castor oil; $C_{5-29}$ mono-glycerides and ethoxylated derivatives thereof; $C_{15-60}$ diglycerides and polyoxyethylene derivatives thereof having 1 to 90 POE groups; $C_{10-40}$ esters (10–40 carbon atoms in the alcohol) of long chain fatty acids(fatty acids having 16 carbon atoms and above); $C_{10-40}$ alcohols; sterols such as cholesterol, ergosterol, and $C_{2-24}$ esters thereof; $C_{8-96}$ ethoxylated fatty esters; $C_{14-130}$ sucrose fatty esters; and $C_{20-130}$ sorbitol and sorbitan monoesters, diesters, and triesters, and polyoxyethylene (POE) derivatives thereof having 0 to 90 POE groups, e.g., polyoxyethylene sorbitan monooleate, sorbitol hexaoleate POE (50). Of these, mono- and di-glycerides, or mixtures thereof, are preferred as low HLB surfactants and the sorbitol and sorbitan compounds as high HLB surfactants. More specifically, preferred low HLB surfactants include $C_9$ to $C_{13}$ monoglycerides (HLB about 4–7), $C_{19}$ to $C_{25}$ diglycerides of mono and poly unsaturated fatty acids (HLB about 3–5), $C_{15}$–$C_{23}$ diglycerides (HLB about 4–6), and $C_{35}$ to $C_{47}$ diglycerides of mono and poly unsaturated fatty acids (HLB about 2.5–4.5); preferred high HLB surfactants include ethoxylated castor oil (HLB about 10–16) and the sorbitan surfactants with HLB from about 10–18. Short chain monohydroxyl alcohols, such as $C_1$ to $C_6$ are not employed as surfactants in these systems due to toxicity factors.

As stated above, the molecular weight of these surfactants is not critical, but it is desirable that at least one of them have a molecular weight of at least about 500, more preferably greater than about 750.

The water-soluble active material to be incorporated in the internal aqueous phase of the w/o microemulsion may be any biologically active material, particularly water-soluble proteins, peptides and other pharmaceutically-active compounds, i.e., drugs, and compounds which may have use as diagnostic agents. Vitamins and other food supplements which are not commonly defined as being "therapeutic" are not within the definition of the active agent. Illustrations of proteins which may be advantageously formulated, particularly for prolonged storage, include enzymes, such as horseradish peroxidase, alkaline phosphatase and derivatives thereof; and other unstable proteins which tend to undergo inactivation during storage at elevated temperatures, such as cytokines, hemoglobin, interleukins, and the like. Peptides including polypeptide hormones such as calcitonins, insulins, and the like are suitable for incorporation.

Other active agents that can be used in the w/o microemulsion system include peptides which may be satisfactorily employed include such pharmaceutically-active peptide drugs as desmopressin (1-desamino-8-D-arginine vasopressin). Drugs that can be employed in this system are water soluble drugs which are characterized by having low oral bioavailability. Examples of some of the drugs that can be employed include: anticoagulants, such as heparin or its derivatives; antimicrobials, such as penicillin G, carbenicillin, meziocillin and other poorly absorbed penicillin derivatives; cephalosporins, such as cephalothin, cefoxitin, cefotaxime and other molecules in this series normally administered by injection; antineoplastic drugs, such as fluorouracil, cytarabine, azauridine, thioguanine, vinblastine, vincristine, and bleomycin; anti-inflammatories, such as aurothioglucose and gold sodium thiomalate; and antiparasitic drugs, such as suramin and mebendazole.

Other active agents include RGD peptides, hematoregulatory peptides, vasopressin, collagenase inhibitors, angiotensin inhibitors, mammalian growth hormones, erythropoietins, interleukins (e.g. IL-2, 3, 4 and the like), clotting factors (e.g. factors VII, VIII, IX) colony stimulating factors (e.g. G-CSF, GM-CS, M-CSF), hypothalamic releasing peptides (e.g. growth hormone releasing peptides, gonadotropin releasing factors), interferons, tissue plasminogen activators, atrial natriuretic peptides, tumor necrosis factor, antibodies, antibody fragments, clotting factors, dismutases, vaccine, immunoregulators, HIV protease inhibitors, neurotrophic factors (e.g. nerve growth factors), peptide and protein mimetics, and angiotensin II antagonists.

The present invention also provides for formulations incorporating small peptides, from about 2 to about 10, more preferably from about 2 to about 6 amino acid moieties. One group in particular, the fibrinogen receptor antagonists (RGD containing peptides) are tetrapeptides with an average molecular weight of about 600. These peptide antagonists are highly potent platelet aggregation inhibitors at plasma levels as low as 1 pmol/ml. A preferred fibrinogen antagonist is the peptide cyclo(S,S)-$N^\alpha$-acetyl-Cys-($N^\alpha$-methyl)Arg-Gly-Asp-Pen-$NH_2$ (SEQ ID NO:1) prepared by the method of Ali et al., published application EP 0 341 915 whose disclosure is herein incorporated by reference in its entirety. Also preferred is the peptide cyclo(S,S)-(2-mercapto)benzoyl-($N^\alpha$-methyl)Arg-Gly-Asp-(2-mercapto)phenylamide which may be prepared by the method disclosed in published EPO 0423212, Application No. 90311537.6 whose disclosure is herein incorporated by reference in its entirety. The RGD peptides can generally be included in the microemulsion in an amount up to about 50 mg/ml of the aqueous phase.

Other fibrinogen antagonists useful in the present invention are those peptides disclosed in Pierschbacher et al., WO 89/05150 (US/88/04403); Marguerie, EP 0 275 748; Adams et al., U.S. Pat. No. 4,857,508; Zimmerman et al., U.S. Pat. No. 4,683,291; Nutt et al., EP 0 410 537; Nutt et al., EP 0 410 539; Nutt et al, EP 0 410 540; Nutt et al., EP 0 410 541; Nutt et al., EP 0 410 767; Nutt et al., EP 0 410 833; Nutt et al., EP 0 422 937; Nutt et al., EP 0 422 938; Alig et al., EP 0 372 486 Ohba et al., WO 90/02751 (PCT/JP89/00926);

Klein et al., U.S. Pat. No. 4,952,562; Scarborough et al., WO 90/15620 (PCT/US90/03417); Ali et al., WO 91/07429 (PCT/US 90/06514), filed Nov. 2, 1990; peptide like compounds as disclosed in Alig et al., EP 0 381 033; and Alig et al., EP 0 384 362; and the cyclic RGD peptides (SEQ ID NO:1 and SEQ ID NO:2, respectively):

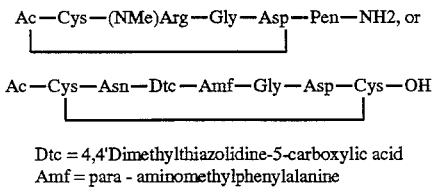

Dtc = 4,4'Dimethylthiazolidine-5-carboxylic acid
Amf = para - aminomethylphenylalanine Larger peptides/polypeptide also useful in the present invention are those disclosed in Pierschbacher et al., U.S. Pat. No. 4,589,881 (>30 residues); Bittle et al., U.S. Pat. No. 4,544,500 (20–30 residues); and Dimarchi et al., EP 0 204 480 (>34 residues).

Also preferred are growth hormone releasing peptides, which are peptides generally of twelve amino acids or less and effect the release of growth hormone. The growth hormone releasing peptides can be used in an amount up to about 75 mg/ml of the aqueous phase.

Exemplary of the class of growth hormone releasing peptides is the peptide His-D-Trp-Ala-Trp-D-Phe-Lys-$NH_2$ and other peptides which cause the release of growth hormone by essentially the same mechanism as His-D-Trp-Ala-Trp-D-Phe-Lys-$NH_2$. Another preferred growth peptide is Ala-His-D-Nal-Ala-Trp-D-Phe-Lys-$NH_2$. Growth hormone releasing peptides are disclosed, for instance, in Momany, U.S. Pat. No. 4,411,890; Momany, U.S. Pat. No. 4,410,513; Momany, U.S. Pat. No. 4,410,512; Momany, U.S. Pat. No. 4,228,158; Momany, U.S. Pat. No. 4,228,157; Momany U.S. Pat. No. 4,228,156; Momany, U.S. Pat. No. 4,228,155; Momany, U.S. Pat. No. 4,226,857; Momany U.S. Pat. No. 4,224,316, Momany U.S. Pat. No. 4,223,021; Momany, U.S. Pat. No. 4,223,020; Momany, U.S. Pat. No. 4,223,019; Bowers et al., U.S. Pat. No. 4,880,778; Bowers et al., U.S. Pat. No. 4,880,777; Bowers et al., U.S. Pat. No. 4,839,344; Bowers et al., U.S. Pat. No. WO 89/10933 (PCT/US89/01829); Bowers et al., EP-A 398 961, Bowers et al. EP-A 400 051, all of which are fully incorporated herein by reference.

The pharmaceutically-active compounds employed in the present invention also include immunogens which can be incorporated into vaccine adjuvant systems. The immunogens which are acceptable include purified proteins and peptides and derivatives thereof, and generally immunogens which have a weight average particle size in the range up to about 150 nm which therefore are capable of being maintained in the aqueous phase of the microemulsion.

The biologically active material is said to be a "water-soluble" material. Those skilled in the art will readily understand by the list of representative active materials that they are soluble to an effective extent in an aqueous phase and have negligible solubility in an organic phase. The solubility of the active materials in the aqueous phase at about 20° C. is at least about 1 part per 100,000 parts and preferably at least about 1 part per 10,000 parts. To achieve this level of solubility the pH or ionic strength of the aqueous phase may be altered. The solubility of the active materials in organic materials, such as those stated comprising the organic phase of the microemulsion, at about 20° C. is less than about 10 parts per 1,000,000 parts and preferably less than about 1 part per 1,000,000 parts. The water:oil partition coefficient is greater than 10:1, advantageously at least about 50:1, preferably at least about 100:1, and most preferably greater than about 1000:1. The water:oil partition coefficient is a commonly used quantity and refers to the ratio of the solubility of the material in water at about 20° C. to the solubility of the material in a reference oil, generally olive oil which is a mixture of triglycerides of saturated and unsaturated fatty acids esterified to gylcerol, at about 20° C. The partition coefficient is determined by dissolving the active agent in an equal volume of water and olive oil (absent surfactant) and determining the solubility in each phase. As used herein, the reference oil is a U.S.P./N.F. grade olive oil available from various chemical suppliers including Spectrum Chemicals Mfg. Corp., Gardena, Calif.

The amount of active ingredient included in the internal aqueous phase may be varied considerably, depending upon its solubility and activity, the use for which it is intended, the amount of emulsion to be employed, and the like. Generally, as stated above, active ingredients in the amounts of $10^{-9}$ to 100% by weight/volume %, based on the volume of the internal aqueous phase, provide a satisfactory formulation for most applications. The biologically active material will either be soluble in the w/o microemulsion or it will be soluble upon the conversion to the o/w emulsion upon the addition of water to the system.

The w/o microemulsions may be formulated with agents for enhancing mucosal absorption of peptides and proteins. These include bile salts such as trihydroxy bile salts, i.e. cholate, taurocholate, and glycocholate, dihydroxy bile salts, i.e. deoxycholate, taurodeoxycholate, chenodeoxycholate, and ursodeoxycholate, triketo bile salts such as dehydrocholate. Non-ionic surfactants such as polyoxyethylene ethers with alkyl chain lengths from 12–18 carbon atoms and polyoxyethylene (POE) chain lengths from 2–60, p-t-octylphenoxypolyoxyethylenes with 2–60 POE groups, nonylphenoxypolyoxyethylenes with 2–60 POE groups, polyoxyethylene sorbitan esters with 8–24 alkyl chain lengths and 4–80 POE groups, and 1-dodecylhexahydro-2H-azepin-2-one (azone, laurocapram) can be used. Anionic surfactants such as sodium dodecyl sulfate and dioctyl sodium sulfosuccinate can be used. Lysolecithins containing saturated fatty acyl chains having 8–24 carbon atoms or unsaturated fatty acyl chains having 1 to 4 double bonds and 16–24 carbon atoms can be used. Mono/diesters of glycerol, such as medium chain fatty acid mono/di-esters containing saturated fatty acids with 8–12 carbon atoms, and mono/diglycerol esters of unsaturated fatty acids having 1 to 4 double bonds and 16–24 carbon atoms can be used. Acylcarnitines, acylcholines and acylamino acids can be used, such as acylcarnitines having 12–20 carbon acyl groups and where the acyl groups have 0–4 double bonds, acylcholines such as acyl choline esters of fatty acids having 8–22 carbon atoms and 0–4 double bonds, and acylamino acids such as N-acyl amino acids and dipeptides having acyl groups with 8–24 carbon atoms and 0–4 double bonds and the amino acids having α or β amino groups and a molecular weight less than 350. Additionally, mono and polyunsaturated fatty acids and their salts having 14–24 carbon atoms and 1–4 double bonds, and salicylic acid and its sodium salt, sodium 5-methoxy-salicylate can be used.

The w/o microemulsions of this invention may readily be prepared by simply mixing together with mild agitation the selected components in the desired ratios at room temperature or at slightly elevated temperatures. As pointed out above, no high-energy mixing or application of heat is necessary, although limited use of each may be employed, if desired, to increase the rate of formation of the microemulsion. Moreover, the ingredients do not have to be added in any particular order other than that the active material be present in the aqueous phase as the emulsion is formed. Preferably, however, the surfactant should first be mixed with the oil phase, followed by the addition of water in the proper ratio. It is preferred to dissolve the active material in the water first, and then add this aqueous phase to the oil and surfactant components.

The size of the droplets, i.e., the number average diameter, in the resulting w/o microemulsion is usually 10–150 nanometers (nm), usually below 50–100 nm, with the majority of droplets below 100 nm, more preferably below 75. The particle size measurement is usually determined by laser light scattering techniques. The water-in-oil microemulsions are also characterized by their stable, clear homogeneous appearance.

The amount of water or aqueous fluid, e.g. aqueous body fluid, necessary to convert the w/o emulsion to an o/w emulsion when used, for example, for storing proteins, is not critical and may be determined routinely by titration of the microemulsion with excess water. Generally, however, it has been found that water in excess of about 1 to 33 times that of the volume of the emulsion is sufficient for this purpose.

Besides the volume of water added or provided by the body itself, other factors which control the rate of release of any given drug include pH, temperature, and degree of agitation. Those skilled in the art will recognize that by varying these conditions in a generally known manner, the release of the drug can be slowed or increased as desired.

The microemulsion system of the present invention can be formulated with a high melting oil, that is, an oil with a melting point above room temperature (22°–23° C.), preferably above about 30° C., in order to formulate a microemulsion which is a solid at room temperature. Also, high melting surfactants such as a $C_{10-40}$ ester of a long chain fatty acid and alcohols having at least about 12 carbon atoms, wherein these surfactants have melting points above room temperature, preferably above about 30° C. Preferably, the microemulsion will melt at body temperatures, generally between about 35°–40° C. The amount of high melting oil and the melting point of that oil can vary, but the final composition containing the microemulsion is solid at room temperatures. The solid microemulsion system can be used as a suppository transport vehicle or as an oral transport vehicle. The oral formulation is preferably in tablet or capsule form. The microemulsion can either be formulated directly with the high melting oil, or the microemulsion can be formulated first, after which the high melting oil is blended with the microemulsion. Such high melting oils are well known in the art and include, for example, partially hydrogenated coconut oils, palm oils, cocobutter, hydrogenated peanut oil, and various hydrogenated vegetable oils, along with combinations thereof. Preferred oils include hydrogenated coconut and palm oils and mixtures thereof.

The w/o microemulsion system that is solid at room temperature (22°–23° C.) can be prepared using the high melting oil directly with the other components during formulation. The solution of components is heated to a slightly elevated temperature of from about 25°–60° C., preferably about 30°–50° C., during mixing and cooled to a solid at room temperature. The final w/o microemulsion system has component ranges within those previously stated for the liquid microemulsion systems. Preferred solid systems have from about 20–90%, preferably 30–60% w/w of a high melting oil having a melting point from about 85°–120° F.; from about 1–50%, preferably 3–30% w/w of the aqueous phase, and 15–80%, preferably 23–60% w/w of a surfactant or surfactant mixture having an HLB range as set forth in this invention. Preferably, the surfactant is a mixture of surfactants containing 5–30%, preferably 8–20% w/w (of the microemulsion) of a surfactant having an HLB greater than 8, and 10–50%, preferably 15–40% w/w (of the microemulsion) of a surfactant having an HLB lower than 8.

The w/o microemulsion system that is solid at room temperature can also be prepared by first preparing the w/o microemulsion without the high melting oil and dispersing this microemulsion in the high melting oil. First, the w/o microemulsion is prepared according to the present invention. Then, the high melting oil is blended with the w/o microemulsion. Commonly this is accomplished at slightly elevated temperatures between about 25°–60° C., preferably about 30°–50° C. The microemulsion is thereby dispersed within a matrix made of the high melting oil. The amount of high melting oil to microemulsion ranges from about 0.5:1 to about 2:1. This amount can vary beyond these ranges so long as a final dispersed microemulsion system is produced which is a solid at room temperature. The high melting oil is typically admixed with a low HLB surfactant, generally having a HLB below about 8, prior to addition to the microemulsion in order to properly retain and disperse the microemulsion in the high melting oil.

It has been surprisingly found that by taking a certain w/o microemulsion system of the present invention, and adjusting it to have a higher effective HLB value, that the w/o microemulsion converts, upon addition of water, not just to an o/w emulsion as do all of the claimed w/o microemulsions, but rather to an o/w microemulsion. The higher HLB value is obtained in the present systems by the addition of a modifier which allows the w/o microemulsion HLB level to be increased beyond its normal stability level without the breaking of the w/o microemulsion. The final HLB level of the surfactant or surfactant mixture of these w/o microemulsions is greater than about 7, and is preferably from about 7 to about 16, most preferably from about 8–13. Modifiers found to be useful are incorporated into the aqueous phase of the microemulsion and include sorbitol, polyethylene glycol (PEG), mannitol, propylene glycol, and mono- and disaccharides. If proteins or peptides are incorporated into the aqueous phase, then preferred modifiers are mannitol, sorbitol, and PEG.

The more modifier added to the w/o microemulsion, the higher the HLB can be raised in the system with the retention of a w/o microemulsion. This higher HLB level allows for conversion to an o/w microemulsion. The precise amount of modifier and the precise amount of higher level HLB surfactant added to the w/o microemulsion is functionally determined by the presence of two end results: (1) the retention of the w/o microemulsion and (2) the conversion to an o/w microemulsion upon addition of water.

The amount of modifier added to the aqueous phase of the w/o microemulsion depends on the desired final HLB. Typically, a 10–50%, preferably a 20–50%, most preferably a 20–30% by weight aqueous modifier solution, preferably a sorbitol solution, can be employed as the modified aqueous phase for the w/o microemulsion. This sorbitol solution can contain physiological buffers and saline or other salts.

The particle size of the w/o microemulsion which converts to an o/w microemulsion is the same as afore-stated for the w/o microemulsions. The number average particle size of the converted o/w microemulsion is typically below about 100 nm, preferably between 10–100 nm, most preferably between 20–60 nm as determined by laser light scattering technique. The amount of water required to convert the w/o system to the o/w microemulsion can vary depending upon the composition of the w/o microemulsion. Typically the amount of water required ranges from about 1 to 10 times the volume of the w/o system. Larger amounts of water can be used to convert the w/o systems, and amounts up to 1000 times the volume of the w/o system, preferably about 3 to about 100 times the volume of the w/o system are used to convert to the o/w microemulsion.

These w/o converting to o/w microemulsion systems can be advantageously employed as transport vehicles for water soluble drugs which degrade in the oil phase, such as certain peptides, proteins, and immunogens used for oral or suppository formulations. Also, these formulations are preferred for intravenous and intraarterial administration. The risk of emboli formation is greatly reduced due to the exceedingly small particle sizes produced upon conversion with excess bodily fluid.

These w/o converting to o/w microemulsion formulations can also be used as nutritional lipid emulsions, and especially as total parenteral nutrition formulations. The w/o system can be converted using an aqueous phase containing water soluble nutrients to form lipid-in-water microemulsions just prior to administration.

The w/o microemulsions containing the biologically active material in the aqueous phase of the present invention are preferably administered parenterally, enterally and via other mucous membranes such as nasally, rectally, vaginally, or via the colon. After administration, the biological effect upon the animal caused by the active material can be measured or observed. The convertible microemulsion system enhances both the drug activation and uptake at the site of conversion. The unique convertibility feature of the present microemulsions provides that the drug will be maintained primarily in the aqueous phase due to oil phase insolubility. This is advantageous in that certain active materials may become inactivated if dispersed within an oil phase or if dissolved within an aqueous phase outside of an emulsion. Generally, such active materials as proteins and peptides employed in the present invention display a greater activity level when stored in the o/w microemulsion system as compared to their being stored for the same period of time and under the same conditions in the same aqueous phase that is not contained within an emulsion system.

The oral administration of a biologically active material, contained within the w/o microemulsion drug delivery system of the present invention, can be in the form of a capsule or tablet. The capsule is generally a starch or gelatin material. Certain active materials may be susceptible to the low pH environment of the stomach and should therefore be delivered to the higher pH environment of the intestinal system. Although such active materials are beneficially delivered in suppository form, if oral delivery is desired, the capsule or tablet can be supplied with an enteric coating. Such coatings are well known in the art as are the methods of enterically coating a capsule or tablet. The method of producing an enterically coated capsule using the w/o microemulsion system of the present invention is as follows. The w/o microemulsion containing the active agent is prepared and this composition is then placed into a capsule. The capsule is then coated with an enteric coating solution. The enteric coating solution contains the polymeric enteric coating substance and solvents. The polymeric enteric coating substance is generally a pharmaceutically acceptable polymer that will dissolve upon contact with intestinal fluids, pH of about 5.5 to 7.0, but will not dissolve in the lower pH stomach fluids. Enteric polymer coatings are readily available commercially, such as the Eastman® C-A-P™ (cellulose acetate phthalate) and C-A-T (cellulose acetate trimellitate) enteric coating materials available from Eastman Chemical Products, Inc. Various techniques are known to apply the entire polymer coating such as spray coating or immersion coating and several layers of the enteric substance may be required.

A preferred w/o microemulsion system for the delivery of a biologically active material, such as calcitonin, to the gastrointestinal tract is one which is both a solid at ambient conditions and which converts into an o/w microemulsion upon contact with an aqueous medium such as bodily fluids. An example of such a preferred system is one containing about 33–45% v/v, most preferably about 36–42%, of a composition containing a mix of triesters:diesters of glycerol and lauric acid having a melting point of about 33°–36° C. (an example being Witepsol H-15 which is a 90:10% wt. mixture of triesters:diesters with a small, less than 2% wt., amount of monoglycerides made by Huls of Germany); about 30–42% v/v, most preferably about 32–40%, of polyoxyethylene sorbitan monooleate (Tween 80, Sigma Corp.); about 5–10% v/v, most preferably about 6–9%, of mono-/di-glycerides of medium chain fatty acids, capric and caprylic (Capmul MCM, from Karlshamns Lipid Specialties, Columbus, Ohio); about 3.5–5.5% v/v, most preferably about 4–5% of a long chain monoglyceride, such as sunflower oil monoglycerides (Myverol 18–92); and about 3–25% v/v, most preferably about 5–20%, of an aqueous 20% w/v sorbitol in buffer solution containing the biologically active material. The drug content, pH, and ionic strength of the aqueous solution will vary depending on the composition that is most suitable for the hosted biological active material. If calcitonin is used, it is preferred to employ up to about 1 mg of salmon calcitonin (from Bachem Co.) per gram of the microemulsion system.

A preferred w/o microemulsion system for the delivery of a biologically active material, such as calcitonin, in a suppository form is one which is a solid at room temperature. An example of such a preferred system is one containing about 23–27% w/w propylene glycol esters of capric/caprylic acids (Captex 200 from Karlshamas Lipid Specialties, Columbus, Ohio); about 6–10% w/w mono- and diglycerides of caprylic/capric acids (Capmul 8210 MCM from Karlshamns Lipid Specialties); about 1–2.5% w/w liquid lecithin from Central Soya (Centrophase 31); about 15–17% w/w polyoxyethylene glycerol triricinoleate (Cremophor EL from BASF); about 40–45% w/w partially hydrogenated palm kernel, coconut and palm oils (HB-108 from Karlshamas Lipid Specialties), and about 5–7% w/w 100 mM acetate buffer, p.H.=4.2. When used in a calcitonin suppository, it is preferred to use about 980 U salmon calcitonin (from Bachem Co.) wherein the weight of the final suppository is about 1.7 g.

Another preferred system for delivery of the active material is a composition containing from about 5–80% v/v of a mixture of triesters:diesters of glycerol and lauric acid having a melting point of about 33°–36° C. (an example being Witepsol H-15); about 15–50% v/v of polyoxyethylene sorbitan monooleate (Tween 80); about 3–11% v/v of mono-/di-glycerides of medium chain fatty acids, capric and caprylic (Capmul MCM); about 2–6% v/v of a long chain monoglyceride, such as sunflower oil monogylcerides (Myverol 18–92); and about 6–42% v/v of an aqueous 25% w/w sorbitol and 25% w/w propylene glycol in buffer solution containing the biologically active material. The drug content, pH, and ionic strength of the aqueous solution will vary depending on the composition that is most suitable for the hosted biological active material. This composition is preferred for the administration of such active agents as calcitonins, insulins, human growth hormones, fibrinogen receptor antagonists (RGD containing peptides, such as cyclo(S.S)-$N^{\alpha}$-acetyl-Cys-($N^{\alpha}$-methyl)Arg-Gly-Asp-Pen-$NH_2$(SEQ ID NO:1)), and growth hormone releasing peptides, such as His-D-Trp-Ala-Trp-D-Phe-Lys-$NH_2$.

As aforestated, in yet another embodiment, our microemulsions may be used to prepare non-drying topical, as opposed to transdermal, salves and ointments. These may readily be prepared by simply admixing a therapeutically-active amount of the emulsion with known topical petroleum bases or the like customarily employed for skin application, as long as these materials are compatible with the emulsion. The w/o microemulsion is ideally suited for wound care treatment where the dry epidermal skin layer, the stratum corneum or horny layer, is removed thereby exposing the aqueous-based dermal skin layer, as for example in burn wounds. The w/o microemulsion can also be used where the dermal skin layer is also partially removed. The w/o microemulsion, when contacted with the dermal or lower body layer converts to an o/w emulsion upon the addition of aqueous bodily fluids. Preferably, proteases, such as serine, metallo, cysteine, aspartyl, and the like which degrade connective tissue proteins such as collagen and elastin and the like, along with growth factors are used as the active material to aid in the removal and repair of skin tissue. Examples of growth factors include, for example, platelet derived growth factor, PDGF, epidermal growth factor, EGF, transforming growth factors, TGFα and TGFβ, and insulin-like growth factor, IGF-I and IGF-II, and the like. These active materials generally have average particle sizes of greater than 1 to about 100, preferably from about 3 to about 30, nanometers. Typically, the molecular weight of these active materials is at least about 5000 and up to over 40,000, preferably from about 5,000 to about 35,000. The average human epidermis pore size is below about 1 nm, and therefore the active materials employed in the topical systems do not effectively traverse the epidermis skin layer.

The topical microemulsion system acts as a resevoir for providing a stable protein to the wound site. The topical microemulsion is preferably presented in the form of a solid, salve, or gel that can be easily removed from the wound site by washing with aqueous fluid. Most preferably, the topical is presented as a solid or semi-solid (deforming upon application of pressure) to maintain the w/o microemulsion at the wound site for conversion and release of the drug.

A further embodiment of the present invention encompasses the use of the w/o microemulsion as a carrier system to be used in a vaccine adjuvant system. In such a vaccine adjuvant system, the immunogen is admixed into the aqueous phase. This aqueous phase is then admixed with the oil phase which contains the surfactant. These adjuvant systems can also be formulated with an immuno-stimulator which are well-known in the vaccine adjuvant art. Such immuno-stimulators include such compounds as muramyl di-or tri-peptide and derivatives thereof; interferons, and interleukins. The aqueous phase may also contain inorganic salts, buffering agents, preservatives, and the like, in addition to the immunogen.

The microemulsion vaccine adjuvant system of the present invention is characterized by its stability and long shelf life, in comparison to emulsion adjuvant systems of the prior art. The use of the oils of the present invention, which are referred to as biodegradable oils, to formulate the microemulsion system provides benefits over previous emulsion adjuvant systems in that the production of granulomas is believed to be decreased. The w/o microemulsion adjuvants can readily convert to oil-in-water emulsions when administered into the body which allows for the generation of macrophage stimulating oil droplets in situ. The smaller and more uniform size of the resulting droplets also is expected to lead to a more reproducible response to a given immunogen.

The invention will now be illustrated by, but is not intended to be limited to, the following examples.

EXAMPLES

Formulation and Convertibility

Several formulations of the water-in-oil (w/o) microemulsions of this invention were prepared in which, by way of illustration, the components, their ratios, and the operating conditions selected to provide a convertible microemulsion, were varied somewhat as shown in the following examples. For convenience, a drug was not included in every instance, but it will be understood that any water-soluble drug, as defined above and as shown in some of the Examples, would be dissolved in the dispersed water phase.

The HLB value of each surfactant system and stability of each emulsion was then determined, as set forth below in each example.

For the purposes of these examples, the HLB values used were those specified by the suppliers of the surfactants; the resulting HLB of a mixture of surfactants was calculated on a volume basis.

In preparing each formulation, the following general procedure was employed:

Into a small vial was pipetted a measured amount of oil, followed by the addition of a surfactant, or mixture of surfactants, of a given HLB value. The vial was then shaken with a vortex mixer for a given number of minutes until the surfactant and oil were evenly mixed. A saline solution was then added to the oil/surfactant mixture and the mixture shaken a few minutes until an optically clear w/o emulsion was recovered. Its stability is measured by periodic visual inspection for the presence of macroscopic phase separation, as shown by cloudiness or the formation of two distinct layers. Stable means the emulsion is clear and single phase.

The physical characteristics of the microemulsions can be tested including such properties as viscosity, conductance and refractive indices.

EXAMPLE 1

In accordance with the foregoing general procedure, a w/o microemulsion was prepared employing the following components, amounts and ratios, and HLB values of the surfactants:

| Component | Composition | HLB Value | Amount (µL) |
|---|---|---|---|
| Oil | Captex 200[1] | | 870.0 |
| Surfactant System | POE 50 Sorbitol Hexaoleate[2] | 11.4 | 50.0 |
| | Cremophor EL[3] | 13.5 | 50.0 |
| Water | Saline (0.9 wt. % NaCl) | | 30.0 |
| TOTAL | | 12.5 | 1000.0 |

[1]Captex 200 - propylene glycol esters of capric/caprylic acids (Karlshamns Lipid Specialties, Columbus, OH)
[2]POE Sorbitol Hexaoleate - polyoxyethylene (50) sorbitol hexaoleate (ICI Americas, Inc. Wilmington, DE)
[3]Cremophor EL - Polyoxyethylenglycerol Triricinoleate 35 DAC (BASF, Inc.)

TABLE 1

Physical and Chemical Characteristics of Captex 200

| | |
|---|---|
| Description: | Diester manufactured by reesterification of fractionated coconut fatty acids (primarily caprylic and caproic) with propylene glycol. |
| CTFA Name: | Propylene glycol dicaprylate/caprate |
| Free Fatty Acid (As Oleic): | 0.03 |
| Hydroxyl Number: | 0.05 |
| Saponification Number: | 329.7 |
| Fatty Acid Composition: | |
| Caproic | 4.1 |
| Caprylic | 68.2 |
| Capric | 27.4 |
| Layric and higher | 0.2 |

These components were mixed in a vortex mixer at 25° C. for about 3 minutes to provide a clear stable w/o microemulsion.

Water was then added to the total composition in the ratio of 4:1 (v/v) to convert the microemulsion to an o/w emulsion.

EXAMPLE 2

In accordance with the procedures of Example 1, the following components were employed to form a w/o microemulsion:

| Component | Composition | HLB Value | Amount (μL) |
|---|---|---|---|
| Oil | Captex 200 | | 870.0 |
| Surfactant | Centrophase 31* | 4.0 | 10.5 |
| System | Cremophor EL | 13.5 | 89.5 |
| Water | Saline (0.9 wt. % NaCl) | | 30.0 |
| TOTAL | | 12.5 | 1000.0 |

*Centrophase 31 - lecithin (mol. wt. - 800) (Central Soya, Fort Wayne, IN).

These components were mixed in a vortex mixer at 25° C. for about 6 minutes to provide a clear w/o microemulsion which was stable, at both 25° C. and 50° C.

Water was then added to the total composition in the ratio of 4:1 (v/v) to convert the microemulsion to an o/w emulsion.

EXAMPLE 3

In accordance with the procedures of Example 2, but substituting 54.5 μL of Tween 80 (polyoxyethylene- sorbitan monooleate, Sigma Corp.) (HLB=15) for Cremophor EL, and increasing the amount of Centrophase 31 to 45.5 μL to provide an average HLB value of 10.0, a w/o microemulsion was formed and converted to an o/w emulsion.

EXAMPLE 4

In accordance with the procedures of Example 1, the following components were employed to form a w/o microemulsion:

| Component | Composition | HLB Value | Amount (μL) |
|---|---|---|---|
| Oil | Captex 200 | | 861.3 |
| Surfactant | Capmul MCM* | 5.0 | 8.7 |
| System | Centrophase 31 | 4.0 | 10.5 |
| | Cremophor EL | 13.5 | 89.5 |
| Water | Saline (0.9 wt. % NaCl) | | 30.0 |
| TOTAL | | 9.0 | 1000.0 |

*Capmul MCM - mono - and diglycerides of medium-chain fatty acids (capric and caprylic) (Karlshamns Lipid Specialties, Columbus, OH).

These components were mixed in a vortex mixer at 25° C. for about 3 minutes to provide a clear w/o microemulsion having a particle size of 25 nm (number average) and a stability from 5° C. to 50° C. as measured by periodic visual inspection.

Water was then added to the total composition in the ratio of 4:1 (v/v) to convert the microemulsion and produce o/w emulsion.

EXAMPLE 5

In accordance with the procedures of Example 2, but increasing the amount of water (saline) from 30 to 150 μL to provide 15% water in the formulation, and adjusting the amounts of the other components accordingly (oil - 350 μL; Centrophase 31 - 52.6 μL; Cremophor EL - 447.4 μL), the w/o microemulsion satisfactorily converted to an o/w emulsion. In this formulation, the ratio of oil-to-water was 2.3:1, and that of surfactant-to-water plus oil was 1:1.

EXAMPLE 6

In accordance with the procedures of Example 4, but altering the amount of Capmul surfactant, first to 4.35 μL (final HLB=10.2), and then to 17.4 μL (final HLB=7.7), convertible microemulsions were also obtained.

EXAMPLE 7

In accordance with the procedures of Example 4, but substituting 8.7 μL of 1-monocapryloyl-rac-glycerol, or 8.7 μL of Dicaprin (an equimolar mixture of 1,2- and 1,3-diglyceride of Capric acid), for the Capmul MCM surfactant, satisfactory convertible microemulsions were also obtained.

EXAMPLE 8

In accordance with the procedures of Example 2, but substituting Myverol 18–92 (glycerol monolinoleate; HLB value - 3.8–4.0) for the Centrophase 31 surfactant of that surfactant system, and mixing the components for 3 minutes, there was obtained a w/o microemulsion which, when water was added (4:1 v/v), converted to an o/w emulsion. The HLB of the surfactant mixture in this formulation was 9.0.

EXAMPLE 9

In accordance with the procedures of Example 4, but substituting 861.3 μL of Myvacet (1-oleyl-2,3-diacetyl glycerol); (Eastman Chemical Products, Inc., Kingsport, Tenn.) for the Captex 200 as the oil, there was obtained a satisfactory w/o microemulsion which, upon addition of water to the total composition (in the ratio of 4:1 v/v), converted to an o/w emulsion. The HLB of the surfactant mixture in this formulation was 9.0.

Stability Data

In order to demonstrate the stability of the compositions of this invention at elevated temperatures for purposes of storing the same for long periods of time, a series of microemulsions was prepared in accordance with this invention, following the general procedures of Example 2. In Example 10, the protein horseradish peroxidase (HRP), was stored for given times and temperatures, then assayed in vitro, as shown in this example.

EXAMPLE 10

This example illustrates the incorporation of a protein, namely the enzyme horseradish peroxidase (HRP), in the convertible w/o microemulsion of this invention, and the stability of this resulting emulsion.

In accordance with the general procedures above, an enzyme-containing microemulsion was prepared from the following components:

| Component | Composition | HLB Value | Amount (μL) |
|---|---|---|---|
| Oil | Captex 200 | | 861.3 |
| Surfactant | Capmul MCM | 5.0 | 8.7 |
| System | Centrophase 31 | 4.0 | 10.5 |
| | Cremophor EL | 13.5 | 89.5 |
| Peroxidase Solution | (see Footnote 1) | | 30.0 |
| TOTAL | | 9.0 | 1000.0 |

1 Peroxidase solution - 100 μL of HRP stock solution (1 mg/ml) in 400 μL of 0.9 wt. % saline (NaCl) solution.

These components were mixed in a vortex mixer at 25° C. for about 2 minutes to provide a w/o microemulsion.

After storage for the specified time at 50° C., the microemulsion was then converted to an o/w emulsion by the addition of water. This was achieved by pipetting 30 μL of the microemulsion containing the horseradish peroxidase enzyme into 970 μL of 0.9 wt.% saline (NaCl) solution.

After conversion, the emulsion was then assayed for activity. This activity was compared with the activity of stock solutions of HRP which had been maintained at 50° C. for the same time and then pipetted into saline (30 μL into 970 μL of saline) in the same manner as the microemulsion above. The stock HRP was first diluted to the same HRP concentration as in the aqueous phase of the converted microemulsion.

A. Assay Procedure

The assay was carried out as follows:

1. Set spectrophotometer at 492 nm and 25° C.
2. Into the cuvette, pipet 2.97 mL OPD (O-phenylene diamine) buffer solution (1 tab.→26 mL)
3. Establish blank at 492 nm.
4. Into the cuvette, pipet 25 μL diluted control HRP solution. Mix and record the increase in absorbance at 492 nm for 5 minutes.
5. Same procedure is followed for microemulsion w/HRP solution. OPD=O-phenylene diamine B. Results:

Percent activity was determined by using the following equation:

$$\text{Percent Activity} = \frac{\text{Activity at time } t}{\text{Activity at time 0}} \times 100$$

The following table summarizes the results that were obtained from the assay for both Control HRP and microemulsion containing HRP.

TABLE 2

PERCENT ACTIVITIES OF BOTH CONTROL HRP
(STOCK SOLUTIONS)
AND MICROEMULSION CONTAINING HRP

| Time (Hours) | % Activity | |
|---|---|---|
| | Control HRP | HRP in ME |
| 0 | 100 | 100 |
| 3 | 76 | 77 |
| 6 | 73 | 83 |
| 24 | 20 | 68 |
| 27 | 20 | 68 |
| 48 | 11 | 53 |

From the foregoing results, it will be seen that after hours, the microemulsion containing HRP was much more active than the control HRP, which had lost most of its activity by 48 hours. Thus, the microemulsion of this invention provides the distinct advantage of permitting long-term storage of proteins at elevated temperatures, whereas heretofore they had to be maintained at much colder temperatures to preserve their stability.

EXAMPLE 11

A series of experiments was carried out in rats using the w/o microemulsions of this invention to evaluate them as a vehicle for the rectal delivery of the peptide calcitonin, (used in the treatment of hypercalcemia by lowering Ca++serum levels), whereby the body fluids of the rat would serve to convert the microemulsion to an o/w emulsion and thus release the calcitonin.

Formulations were produced which ranged from 3% to 15% (v/v) aqueous phase and which ranged from liquids to gels at room temperature. The formulations contained, in addition to the aqueous phase, one to three oils and a blend of two emulsifiers. Most formulations showed temperature stability over the range from 5° C. to 50° C. Three formulations with different oil blends were chosen for biological evaluation in juvenile, male rat model (Sprague-Dawley rats; 140–170 gm).

Rectal installation was compared with direct injections of calcitonin into the body. As shown by the data below, rectal instillation of each of the three microemulsion calcitonin formulations tested produced a dose dependent lowering of serum calcium in the rat, thereby demonstrating that the w/o microemulsion had been converted in the colon, with the release of effective amounts of active calcitonin. Control microemulsion preparations, on the other hand, which did not contain calcitonin, did not produce a significant change in serum calcium levels. Moreover, as shown below, incorporation of two oils plus coconut oil into the suppository to form a semi-solid microemulsion improved the calcitonin response by more than tenfold over the basic liquid formulation containing a single oil.

A. Formulations

Three w/o microemulsion formulations were tested which contained 3% v/v aqueous phase volume, and varying amounts of calcitonin/ml of emulsion. Two, Formulations A and B below, were formulated as liquids; the third microemulsion (Formulation C) was formulated in semi-solid (suppository) form by addition of a high-melting coconut oil to the microemulsion. This formulation was a soft waxy solid at room temperature which melted at body temperature to release calcitonin via the microemulsion.

Key to Calcitonin Microemulsions Formulations:

A. The microemulsion of Example 2, plus calcitonin.

B. The microemulsion of Example 4, plus calcitonin.

C. The microemulsion of Example 4, (1 volume,); to which is added 2 volumes of a mixture containing 1.8 volumes coconut oil and 0.2 volume Capmul MCM; plus calcitonin.

All calcitonin concentrations are given in units of biological activity per volume of final emulsion.

B. Test Methods

The calcitonin-containing, or just saline-containing, (control) microemulsions were administered rectally to each of a group of 3 to 7 rats in a volume of 250 μL. Blood samples were taken at time=0, 1, and 2 hours after dosing. Serum calcium was measured after 1 and 2 hours because initial studies showed that this is when maximal calcitonin response was obtained. The rats were anaesthetized throughout the entire procedure and were bled via the orbital sinus.

Serum was prepared from each blood sample and serum $Ca^{+2}$ (free ionized calcium) levels were determined using a Beckman calcium clinical assay kit.

C. Results

The results of this study are shown in Table 2 which summarizes the activity of Microemulsions A, B and C.

TABLE 3

EFFECT OF RECTALLY-INSTILLED CALCITONIN MICROEMULSIONS ON SERUM CALCIUM LEVELS

| Micro-emulsion | Calcitonin Content (units/ml) | No. of Animals | Change in Serum $Ca^{+2}$ at 1 Hr. after Treatment (mg/dL) ± SD[1] | After 2 Hrs.[1] |
|---|---|---|---|---|
| A | 0 | 4 | 0.23 ± 2.55 | 1.92 ± 1.01 |
|  | 60 | 7 | −1.81 ± 2.50 | −1.02 ± 1.65 |
|  | 120 | 5 | −1.11 ± 0.96 | −1.60 ± 1.25 |
|  | 240 | 5 | −1.89 ± 1.27 | −2.44 ± 1.29 |
| B | 0 | 4 | −0.38 ± 1.58 | 0.73 ± 0.91 |
|  | 10 | 4 | −1.78 ± 0.78 | −1.30 ± 0.50 |
|  | 20 | 5 | −1.98 ± 0.47 | −2.36 ± 0.44 |
| C | 0 | 3 | 0.17 ± 0.09 | 0.67 ± 0.50 |
|  | 10 | 4 | −1.71 ± 0.51 | −2.39 ± 0.36 |
|  | 20 | 4 | −1.82 ± 0.35 | −2.23 ± 0.11 |
| Preconverted | 0 | 5 | 0.41 ± 0.13 | 0.47 ± 0.40 |
| B | 20 | 5 | −1.27 ± 1.07 | −1.62 ± 1.29 |
| Saline | 10 | 5 | −0.13 ± 0.45 | 0.15 ± 0.33 |

[1]Ionized calcium in blood serum in units of milligrams of calcium (mg) per deciliter (100 mL) of serum ± the standard deviation.

The results shown in Table 2 show the effectiveness of our microemulsions containing calcitonin in lowering serum calcium. Because of the higher response of ME-B compared to ME-A, we needed to determine that the lower response of ME-A was not due to deactivation of the calcitonin by the formulation itself. To determine this, 250 µL of ME-A (60 Units/mL) and ME-A (0 Units/mL) were injected SQ into 2 pairs of animals. The serum calcium fell an average of 3.2 mg/dL (milligrams/deciliter) in the calcitonin microemulsion-treated animals, and 0.3 mg/dL in the controls. This demonstrates the presence of active calcitonin in ME-A.

Another series of tests were performed to demonstrate the efficacy of these emulsions which were converted after storage but before administration into the rats. In accordance with these tests, Microemulsion B was formulated and stored at 5° C. for 2 days, following which it was converted to an o/w emulsion by addition of water equal in amount to that of the total volume of the emulsion prior to rectal introduction into rats. As shown in Table 2, the calcitonin was generally effective after storage when pre-converted and then used, but not as effective as internal conversion within the colon.

The table also shows that incorporation of the mono- and diglycerides surprisingly produced a significant improvement in the response to calcitonin. A dose of 20 U/mL of ME-B produced a response similar to that previously obtained at 240 U/mL of ME-A, more than an order of magnitude improvement.

Rectal administration of the solid calcitonin microemulsion C produced responses that were equal to or greater than those seen with the B formulation.

The last line of Table 2 indicates that instilling a saline solution of calcitonin into the rectum produced no significant response.

EXAMPLE 12

The following example demonstrates that a non-convertible microemulsion wherein the surfactant HLB was 4.0, which was not effective in the rectal delivery of calcitonin.

A microemulsion was formulated as follows, using the general procedure of Example 1:

| COMPONENT | COMPOSITION | HLB VALUE | AMOUNT (µL) |
|---|---|---|---|
| Oil | Captex 200 |  | 500 |
| Surfactant | Centrophase 31[1] | 4.0 | 450 |
| Water Plus | Buffered Solution 2 |  | 50 |
| Calcitonin |  |  |  |
| Total |  | 4.0 | 1000 |

[1]Liquid Soybean Lecithin
[2]Calcitonin amount = 240 units/mL

The resulting calcitonin-containing w/o microemulsion was introduced into the colons of rats in accordance with the general procedures of Example 11. A measurement of the ionized calcium in the blood showed no significant decrease for the microemulsion system when compared to a control formulation with no calcitonin.

EXAMPLE 13

The following example demonstrates the production of w/o microemulsion systems which have relatively high water concentrations. In accordance with the above mentioned general procedure, w/o microemulsions were prepared employing the following components, amounts and ratios (volumes below are in microliters):

|  | Surfactant | | | Oil | | Aqueous Phase | |
|---|---|---|---|---|---|---|---|
| Example | Myverol 18-92 | Tween 20 | Centrolene A | Captex 200 | Triacetin | 1% NaCl Solut. | Water |
| 1 | 270 | 230 | — | 100 | — | 400 | — |
| 2 | 250 | 200 | 50 | 100 | — | 400 | — |
| 3 | 240 | 180 | 80 | 50 | 50 | — | 400 |
| 4 | 260 | 160 | 80 | 50 | 50 | — | 400 |
| 5 | 260 | 160 | 80 | 50 | 50 | — | 500 |
| 6 | 260 | 160 | 80 | 50 | 50 | — | 600 |
| 7 | 260 | 160 | 80 | 50 | 50 | — | 720 |

Tween 20 is a laurate ester of sorbitol having a HLB value of about 16.7 purchased from Spectrum, New Brunswick, N.J. Centrolene A is a hydroxylated lecithin having a HLB value of about 9.5 manufactured by Central Soya, Fort Wayne, Ind..

EXAMPLE 14

A series of experiments was carried out using rats with the w/o microemulsion of this invention that are solid at ambient conditions to evaluate them as a vehicle for the oral delivery of the peptide salmon calcitonin (used in the treatment of hypercalcemia by lowering $Ca^{2+}$ and $PO_4$ serum levels). The body fluids of the rat served to convert the microemulsion to an o/w emulsion which activated the drug and promoted drug uptake by the animal. The monitored variables were $Ca^{2+}$ and $PO_4$.

Formulations

The test preparations were prepared using a high melting point oil, in this case a mixture of hydrogenated coconut and palm oil. The oils used were obtained from Karlshamns Lipid Specialties, USA, of Columbus, Ohio. The oils were labeled HB-95, HB-108, and HB-118 which corresponded to the trade names of HYDROKOTE 95, 108, and 118. The oils had an approximate melting point of 95°, 108°, and 118° F. respectively.

The A group microemulsions were prepared by first formulating the microemulsion and then admixing the HB-108 oil with the microemulsion. The microemulsion components were mixed in a container at an elevated temperature of about 40° C. to which was added the calcitonin contained in the acetate buffer. Once the microemulsion was formed, the HB-108 component containing 10% Capmul was added.

The B and C group microemulsions were prepared by formulating the microemulsion directly with the HB oil.

FORMULATIONS

| | Group A1 | Control (A1') |
|---|---|---|
| Dose | 40 U/mL | 0 U/ml |
| 10% Capmul MCM in Captex 200 | 570 uL | 1.71 mL |
| Cremophor EL | 298 uL | 894 uL |
| Lecithin | 35 uL | 105 uL |
| 100 mm acetate buffer | 92 uL | 300 uL |
| calcitonin stock sol'n 10,000 U/mL | 8 uL | — |
| Total ME | 1.0 mL | 3.0 mL |
| 10% Capmul in HB-108 | 1.0 mL | 3.0 mL |
| Total volume | 2.0 mL | 6.0 mL |

| | Group B1 | Control (B1') |
|---|---|---|
| Dose | 40 U/mL | 0 U/ml |
| Myverol 18-92 | 373 uL | 746 uL |
| Tween 80 | 404 uL | 808 uL |
| Capmul MCM | 124 uL | 249 uL |
| HB-95 | 725 uL | 1.45 mL |
| 100 mm acetate buffer | 365 uL | 746 uL |
| calcitonin stock sol'n 10,000 U/mL | 8 uL | — |
| Total volume | 2.0 mL | 4.0 mL |

-continued

| | Group C1 | Control (C1') |
|---|---|---|
| Dose | 40 U/mL | 0 U/ml |
| Myverol 18-92 | 373 uL | 746 uL |
| Tween 80 | 404 uL | 808 uL |
| Capmul MCM | 124 uL | 249 uL |
| HB-118 | 725 uL | 1.45 mL |
| 100 mm acetate buffer | 365 uL | 746 uL |
| calcitonin stock sol'n 10,000 U/mL | 8 uL | — |
| Total volume | 2.0 mL | 4.0 mL |

Test Method

Each test group contained five animals (juvenile male rats, Spraque-Dawley rats approx. 140–170 gm). Group A1, B1 and C1 received 250 uL of the respective microemulsion, 40 U/ml calcitonin; the controls received 250 µL of the control microemulsion.

The animals were orally garaged with melted microemulsion and then quickly anaesthetized and a blood sample was taken via the orbital sinus to establish a baseline ($T_o$). After 120 min., a second blood sample was taken. The $Ca^{2+}$ and $PO_4$ levels were analyzed in both samples and compared to determine the activation and uptake of the drug. Serum $Ca^{2+}$ (free ionized calcium) levels were determined using a Beckman 700 calcium clinical assay kit along with serum $PO_4$ levels.

Results

The results of this study are shown in the table below which summarizes the activity of microemulsions A1, B1, and C1 and the controls A1', B1', and C1'. All microemulsion calcitonin formulations showed statistically significant reductions in both $Ca^{2+}$ and $PO_4$ serum levels, except that the C1 emulsion system did not show such activity for reduction of $Ca^{2+}$. The 'P' value is a statistical quantity that refers to the probability that the treatment and control values are equal. A 'P' value of 0.05 represents a one-in-twenty chance that the groups are equal. Therefore, 'P' values below 0.05 are considered statistically significant.

SUMMARY OF SERUM CALCIUM AND PHOSPHATE CHANGES INDUCED BY
ORAL GAVAGE OF RATS WITH MICROEMULSIONS CONTAINING HIGH MELTING
POINT TRIGLYCERIDES WITH OR WITHOUT CALCITONIN

| Formulation | Triglyceride | Calcitonin MRC U/mL | $Ca^{2+}$ Diff. mg/dL vs. 2 Hr | 'P' Value Calcitonin vs. Control | $PO_4$ Diff. mg/dL vs. 2 Hr | 'P' Value Calitonin vs. Control |
|---|---|---|---|---|---|---|
| A1  | HB-108 | 40 | −0.62 | —     | −2.8 |       |
| A1' | HB-108 | 0  | −0.14 | 0.029 | −0.8 | 0.010 |
| B1  | HB-95  | 40 | −1.58 | —     | −2.6 |       |
| B1' | HB-95  | 0  | 0.82  | 0.036 | −0.2 | 0.003 |
| C1  | HB-118 | 40 | 2.08  | —     | −2.6 |       |
| C1' | HB-118 | 0  | 0.08  | 0.880 | 0.0  | 0.005 |

'P' Values < 0.05 are considered significant

EXAMPLE 15

A series of experiments was carried out using rats with the w/o microemulsion of this invention to evaluate the performance between solid formulations and liquid formulations using the peptide salmon calcitonin (used in the treatment of hypercalcemia by lowering $Ca^{2+}$ serum levels) via oral administration. The body fluids of the rat served to convert the microemulsion to an o/w emulsion which activated the drug and promoted drug uptake by the animal. The serum $Ca^{2+}$ was monitored to evaluate the effectiveness of the microemulsion carrier system.

Formulations

The solid test preparations were prepared using a high melting point oil, in this case a mixture of hydrogenated coconut and palm oil, HB-108 (HYDROKOTE 108) which had a melting point of 108° F.

The A and B group microemulsions (ME) were prepared as liquid microemulsions at room temperature. The A ME was the liquid control and did not contain calcitonin. The group B ME was the liquid calcitonin sample. The C and D ME were prepared as solids at room temperature by first formulating the microemulsion and then admixing the HB-108 oil with the microemulsion. The microemulsion components were mixed in a container at an elevated temperature of about 40° C. to which was added the calcitonin contained in the acetate buffer. Once the microemulsion was formed, the HB-108 component containing 10% Capmul was added. The C ME was the control solid ME and the D ME was the calcitonin sample.

| Dose | FORMULATIONS | | | |
|---|---|---|---|---|
|  | Group A Control | Group B 40 U/mL Calcitonin | Group C* Control | Group D* 40 U/mL Calcitonin |
| Capmul MCM | 157 uL | 157 uL | 57 uL | 57 uL |
| Captex 200 | 1.413 mL | 1.413 mL | 513 uL | 513 uL |
| Centrophase 31 (lecithin) | 35 uL | 35 uL | 35 uL | 35 uL |
| Cremophor EL | 298 uL | 298 uL | 298 uL | 298 uL |
| Saline | 100 ul | 92 uL | 100 ul | 92 uL |
| Salmon Calcitonin 10,000 U/mL | — | 8 uL | — | 8 uL |
| HB-108** | — | — | 0.9 mL | 0.9 mL |
| Capmul MCM** | — | — | 0.1 mL | 0.1 mL |
| Total Volumes | 2 mL | 2 mL | 2 mL | 2 mL |

*The suppository base contained small amounts of Methylparaben, Propylparaben and BHT.
**The C and D ME were prepared first and these suppository base components added thereto to formulate the final ME which were solid at room temperature.

Test Method

Each test group contained four animals (juvenile male rats, Spraque-Dawley rats approx. 110 gm). Groups B and D received 250 uL of the respective microemulsion, 10 U/ml calcitonin; the controls received 250 uL of the control microemulsion.

The animals were orally garaged with the liquid ME and melted solid ME and then quickly anaesthetized and a blood sample was taken via the orbital sinus to establish a baseline. After 120 min., a second blood sample was taken. The $Ca^{2+}$ level was analyzed in both samples and compared to determine the activation and uptake of the drug. Serum $Ca^{2+}$ (free ionized calcium) levels were determined using a Beckman 700 calcium clinical assay kit.

Results

The results of this study are shown in the table below which summarizes the activity of microemulsions A, B, C, and D. The serum $Ca^{2+}$ level after 120 min. was found to be significantly reduced, when compared to the control, in only the solid microemulsion formulation, ME D. The serum $Ca^{2+}$ level was not significantly reduced using the liquid calcitonin sample, ME B, when compared to the control.

SUMMARY OF SERUM CALCIUM LEVELS TWO HOURS
AFTER GAVAGE WITH LIQUID OR MELTED SOLID
MICROEMULSIONS WITH OR WITHOUT
SALMON CALCITONIN IN THE AQUEOUS PHASE

| Group | Treatment | Calcitonin MRC U/mL | Serum Ca+2 2 Hr Postdose | SD | 'P' Diff. |
|---|---|---|---|---|---|
| A | Liquid ME | 0  | 13.9 | 2.75 | —     |
| B | Liquid ME | 40 | 12.2 | 0.82 | 0.860 |

SUMMARY OF SERUM CALCIUM LEVELS TWO HOURS
AFTER GAVAGE WITH LIQUID OR MELTED SOLID
MICROEMULSIONS WITH OR WITHOUT
SALMON CALCITONIN IN THE AQUEOUS PHASE

| Group | Treatment | Calcitonin MRC U/mL | Serum Ca+2 2 Hr Postdose | SD | 'P' Diff. |
|---|---|---|---|---|---|
| C | Solid ME | 0 | 13.5 | 2.89 | — |
| D | Solid ME | 40 | 9.0 | 2.70 | 0.033 |

'P' Values < 0.05 are considered significant.

EXAMPLE 16

Stable w/o microemulsion formulations were prepared which, upon conversion with additional water, form o/w microemulsions. The w/o microemulsions were formulated with a sorbitol in saline solution which allowed for the formation of the w/o microemulsion at higher HLB values than those required to form a w/o microemulsion without the presence of the sorbitol solution. The higher HLB value allows for the system to convert into an o/w microemulsion.

Sample w/o microemulsions which convert to o/w microemulsions were prepared according to the systems described below. The HB-95 component is a purified coconut and palm oil mixture manufactured by Karlshamns Lipid Specialties of Columbus, Ohio, having a melting point of 95° F. Myverol 18–92 is a surfactant having an HLB=4 and is manufactured by Eastman Chemicals. Capmul MCM is a surfactant having an HLB=5.5–6.0 and is manufactured by Karlshamns Lipid Specialties. Tween 80 is a surfactant having an HLB=15 and was purchased from Spectrum Chemicals. The sorbitol was dissolved in a saline solution of 0.15M NaCl. The HLB was determined using a volume average. The temperature was the temperature at which the microemulsion was formed.

The number average particle size of the converted microemulsion ranged from about 20 to about 70 nanometers. The amount of water used to convert the w/o microemulsion to the o/w microemulsion ranged from about 10 to about 1000 times the amount of the original w/o microemulsion volume.

Formulations

The test microemulsion systems were prepared as set forth below. Group A was a suppository formulation made with a microemulsion formulation of the present invention. The Group A microemulsion was made first as a liquid and then dispersed within a high melting oil. The other groups were buffer solutions and not microemulsions.

| Group A | |
|---|---|
| Captex 200 with 10% Capmul MCM | 1.14 ml |
| Lecithin | 0.07 ml |
| Cremophor EL | 0.59 ml |
| hGH in sterile H$_2$O | 0.20 ml |
| HB-108 with 10% Capmul MCM | 2.00 ml |

Group A contained 0.096 U hGH/ml. Group B was a 5 mM NaPO$_4$ buffer solution at pH=7.8 with 0.096 U hGH/ml. Group C was a 5 mM NAPO$_4$ buffer solution at pH=7.8 with 0.024 U hGH/ml. Group D contained no hGH and was a 5 mM NaPO$_4$ buffer solution at pH=7.8.

Test Method

Test rats were divided into four groups: A, B, C, and D. Groups A, B, and C received the extracted growth hormone while group D was a control and did not receive the hormone. The rats were approximately 100 grams and were fasted for 24 hours prior to testing.

The dosage and group size is shown in the table below. The injected group, Group C, received the extracted hGH in a buffer solution at the human equivalent dose of 0.05 mg/kg body weight. The two rectal administration groups, Groups A and B, received ten times the human equivalent dose.

| Group | ROUTE | (Vol/dosage form) | [Drug]/rat | No. |
|---|---|---|---|---|
| A | Rectal | 250 ul/supp. | .024 Units | 18 |
| B | Rectal | 250 ul/buffer | .024 Units | 12 |
| C | SQ | 100 ul/buffer | .0024 Units | 12 |
| D | Control | 0 | 0 | 2 |

The rats were anaesthetized just prior to dosing. Suppositories (Group A) and the buffer solution (Group B) adminw/o Converting to o/w Microemulsion Formulations

| Sample ID | HB-95 (µl) | Captex 200 (µl) | Myverol 18-92 (µl) | Capmul MCM (µl) | Tween 80 (µl) | 20% Sorbitol in Saline (µl) | 30% Sorbitol in Saline (µl) | HLB | Temp. (°C.) |
|---|---|---|---|---|---|---|---|---|---|
| A | — | 700 | 130 | 90 | 650 | 360 | — | 12.4 | 25 |
| B | 700 | — | 130 | 90 | 650 | — | 360 | 12.4 | 40 |
| C | 400 | 300 | 140 | 160 | 570 | 460 | — | 11.5 | 37 |
| D | 400 | 300 | 100 | 160 | 610 | 460 | — | 12.0 | 37 |
| E | 400 | 300 | 60 | 160 | 650 | 460 | — | 12.5 | 37 |

EXAMPLE 17

A series of experiments was carried out using rats with the w/o microemulsion of this invention to evaluate them as a vehicle for the delivery of the human growth hormone, hGH. The body fluids of the rats served to convert the microemulsion to an o/w emulsion which activated the drug and promoted drug uptake across the mucosal membrane of the rat colon.

istered rectally were sealed in the rectum by a plug and liquid cement. Group C animals were injected subcutaneously (SQ). After administering the dosage, serum hGH levels were determined at 30, 60, 120, 180, 240, and 300 minutes. Three animals from Group A were used per data point. Two animals from Groups B and C were used per data point. Two animals were used at 0 minutes for a baseline in the control group, Group D. The blood samples were taken from the orbital sinus. The blood was centrifuged and the serum assayed by hGH ELISA (Medix Lab, Foster City, Calif.) for quantitation of the extracted growth hormone.

Results

At ten times the human equivalent dose level, the suppository formulations (Group A) showed an equivalent bioavailability to the injected dose (Group C). The AUC (area under the curve) for both routes of administration was determined using the trapezoid rule (M. Gibaldi, *Biopharmaceutics and Clinical Pharmacokinetics*, Lea and Febiger, Philadelphia, Pa., 1984, pp. 315–16). The AUC was approximately 24.5 ng-hr/ml for both the SQ injection and the suppository. The hGH in buffer that was administered rectally at the same dose as the suppository formulation showed no uptake of the drug. The bioavailability of the suppository formulation was about 10% as compared to an injected dose.

| Time (min) | Injected hGH (Group C) (ng/mL) | SD | Suppository hGH (Group A) (ng/mL) | SD |
|---|---|---|---|---|
| 30 | 16.5 | 5.00 | 16.000 | 4.360 |
| 60 | 10.0 | 0.00 | 14.700 | 8.330 |
| 120 | 6.0 | 1.40 | 2.000 | 2.000 |
| 180 | 2.5 | 2.12 | 1.670 | 1.160 |
| 240 | 0.5 | 0.71 | 1.670 | 0.580 |
| 300 | 0.0 | 0.00 | 0.333 | 0.577 |

Injected n = 2;
suppository n = 3

EXAMPLE 18

Experiments were carried out using rats with the w/o microemulsion of this invention to evaluate them as a vehicle for the delivery of the peptide cyclo(S,S)-$N^{\alpha}$-acetyl-Cys-($N^{\alpha}$-methyl) Arg-Gly-Asp-Pen-$NH_2$ (SEQ ID NO:1).

Formulations

The test microemulsion systems were prepared according to the methods of the application with the peptide added to the system last.

| COMPOSITIONS OF THE MICROEMULSIONS (WEIGHT %) | | | | | | |
|---|---|---|---|---|---|---|
| COMPONENT (WT %) | ME-1 | ME-2 | ME-3 | ME-4 | ME-5 | ME-6 |
| CAPTEX 200 | 68.30 | 76.47 | | 76.57 | 76.65 | 76.49 |
| MYVACET | | | 76.91 | | | |
| CAPMUL MCM | 8.31 | | 9.09 | | 9.28 | 9.26 |
| DICAPRIN | | | | 9.26 | | |
| CENTROPHASE 31 | 1.60 | 1.61 | | 0.96 | 2.13 | |
| MYVEROL 18-92 | | | 1.04 | | | 1.06 |
| CREMOPHOR EL | 16.52 | 16.63 | 9.82 | 10.01 | | 10.00 |
| TWEEN 80 | | | | | 8.74 | |
| SALINE (PEPTIDE) | 5.26 | 5.30 | 3.13 | 3.19 | 3.20 | 3.19 |

Test Method

Intravenous (i.v.) Administration: Fasted rats were anesthetized with an intraperitoneal (i.p.) injection and surgically fitted with a jugular catheter (ACUC protocol #90-151). Rats were allowed to recover from the surgery for 1 day. Catheterized rats were fasted for 18 hr prior to the experiment. Each rat received either a 1 mg or 3 mg peptide/kg dose by lateral tail-vein administration. Blood samples of 0.5 ml aliquots were collected at 0, 1, 3, 5, 10, 15, 30, 45, 60, 90, 120, 150, and 180 min. The 0 min sample was taken 15 min prior to administration of the dose. Plasma was removed from the whole blood by centrifugation at 1600×g for 5 min, and then plasma was stored at –20° C. in 250 µl aliquots per sample. The blood pellet was reconstituted with 12.5 units heparinized saline and returned to the appropriate rat via the jugular catheter. After the experiment, rats were euthanized with i.v. administration of pentobarbital.

Intraduodenal (i.d.) Adminstration: Fasted rats were administered an i.p. injection of anesthesia cocktail and surgically fitted with jugular and duodenal catheters. Rats were allowed to recover from the surgery for 4–5 days (ACUC protocol #91-055). Catherized rats were fasted 18–20 hr prior to the experiment. Each group of rats received either 10 mg peptide/kg in each microemulsion (3.3 ml/kg) or 6.5 mg peptide/kg in each microemulsion (3.3 ml/kg). A saline control was administered to a group of rats containing 10 mg peptide/kg in a saline solution. Blood samples of 0.5 ml aliquots were collected via jugular catheter in heparinized eppendorf tubes at 0, 10, 30, 60, 120, 180, 240, and 1440 min. The 0 min sample was taken 15 min prior to administration of the dose by duodenal catheter. Plasma was collected for analysis and the blood returned to rats as described in the i.v. administration protocol. After 24 hr, rats were euthanized by i.v. administration of pentobarbital, exsanguinated, and a macroscopic observation of the intestinal tract was performed.

Post-Column HPLC Fluorescence Assay: For samples and standards, plasma components were precipitated with 0.6 ml cetonitrile, and then pelleted by centrifugation at 16,000×g for 20 min. The supernatant was removed, and then dried to powder under $N_2$ at 40° C. Powder was dissolved in 0.5 ml 1% TFA solution, and then processed by solid-phase extraction procedure (SPEP). SPEP was as follows: 1) condition 1 ml $C_{18}$ columns with methanol, and then rinse columns with 1 ml water, 2) standards and samples were applied to columns, and then rinsed twice with 1 ml water, 3) standards and samples were collected in tubes upon elution from column with methanol by two 0.5 ml aliquots. The samples and standards were dried to powder under $N_2$ at 40° C., and then dissolved in 100 µl of 10% methanol: 90% ultrapure water solution. Standards and samples were placed in HPLC vials. Vials with standards were placed before and after vials containing the samples for HPLC analysis. For the peptide standards, an aliquot was injected for analysis based on the concentration of the standard as follows: 50 µl aliquot was injected for analysis by post-column fluorescence detection. Fluorescence chromatography data were collected and integrated using Nelson Chromatography Data System. The peak area ratio (Y) and peptide standard concentration (X) were used to determine the slope of a line which was forced through the origin from the equation: slope=(sum of X*Y)/(sum of $X^2$). The slope represented the relationship between peak area ratio and peptide plasma concentration for the samples.

Results

The area under the plasma concentration curve (AUC) was determined for each test group. The percentage bioavailability was determined by the equation with the average AUC from iv administration: $[(AUC_{id}/AUC_{iv})*(mg/kg_{iv}/mg/kg_{id})]*100$. The summary of the results are listed below in which the microemulsion formulations of the present invention showed a significant increase in the bioavailability of the peptide in comparison to the saline solution.

| FORMULATION | DOSE (mg/kg) | N | AUC[1] | BAC[2] (%) |
|---|---|---|---|---|
| SALINE | 10.0 | 3 | 0.011 ± .005 | 0.5 ± 0.3 |
| ME-1 | 6.5 | 3 | 0.405 ± .099 | 29.1 ± 7.1 |
| ME-2 | 6.5 | 3 | 0.269 ± 0.164 | 19.4 ± 11.8 |
| ME-3 | 10.0 | 3 | 0.115 ± 0.042 | 5.4 ± 2.2 |
| ME-4 | 10.0 | 3 | 0.054 ± 0.04 | 2.5 ± 1.9 |
| ME-5 | 10.0 | 1 | 0.8 | 7.4 |
| ME-6 | 10.0 | 3 | 0.308 ± 0.094 | 14.4 ± 4.4 |

[1] Area under the curve (mg * min/ml)
[2] Bioavailability relative to i.v. injected peptide

EXAMPLE 19

A w/o microemulsion according to ME-1 from Example 18 was formulated with the growth hormone releasing peptide His-D-Trp-Ala-Trp-D-Phe-Lys-NH$_2$. The composition of the microemulsion was:

| | |
|---|---|
| Captex 200 | 68.3% w/w |
| Capmul MCM | 8.3% w/w |
| Centrophase 31 | 1.6% w/w |
| Cremophor EL | 16.5% w/w |
| Aqueous | 5.3% w/w |

The aqueous solution contained 25.43 mg peptide/ml.

EXAMPLE 20–24

A w/o microemulsion according to ME-2, ME-3, ME-4, ME-5, and ME-6 from Example 18 is formulated with the growth hormone releasing peptide His-D-Trp-Ala-Trp-D-Phe-Lys-NH$_2$ at both about 25 mg/ml and 75 mg/ml of the aqueous medium.

EXAMPLE 25

Various phase diagrams were prepared by mixing the surfactants in the weight ratios indicated in the following figures and then mixing the surfactant mixture with the oil in various weight ratios. The oil/surfactant mixtures were then titrated with increasing amounts of a 0.9% w/w saline solution. The experiments were carried out at room temperature, 22°–23° C., unless indicated otherwise. The water-in-oil microemulsion regions were stable for at least 24 hours as determined by maintaining a single phase system. The presence of liquid crystalline phases was determined by examination of the samples between crossed polarizers, these systems were not defined in the figures as water-in-oil microemulsions.

The components of the water-in-oil microemulsions are:

Captex 200 - propylene glycol esters of capric/caprylic acids (Karlshamns Lipid Specialties, Columbus, Ohio)

Capmul MCM - mono-2nd diglycerides of medium-chain fatty acids (capric and caprylic) (Karlshamns Lipid Specialties, Columbus, Ohio) (HLB=5.0)

Cremophor EL - polyoxyethylene glycerol triricinoleate 35 DAC (BASF, Inc.) (HLB=13.5)

Myverol 18–92 - glycerol monolinoleate (HLB=3.8–4.0)

Centrophase 31 - lecithin (mol. wt. –800) (Central Soya, Fort Wayne, Ind.) (HLB=4.0)

Tween 80 - polyoxyethylene-sorbitan monooleate, Sigma Corp. (HLB=15)

Whitepsol H-15 - a 90:10% Wt. mixture of triesters: diesters of glycerol and lauric acid with less than 2% wt. monoglycerides, m.p. 33°–36° C.

In FIG. 1, the region defined as "A" is the water-in-oil microemulsion region while the region defined as "B" is a micelle solution region. In FIG. 1, the oil is Captex 200, the aqueous phase is a 0.9% wt. NaCl aqueous solution, and the surfactant mixture is Capmul MCM:Myverol18–92: Cremophor EL in a weight ratio of 45.5:5.2:49.2. ME-6 from Example 18 is included within this phase diagram.

Figure 2:
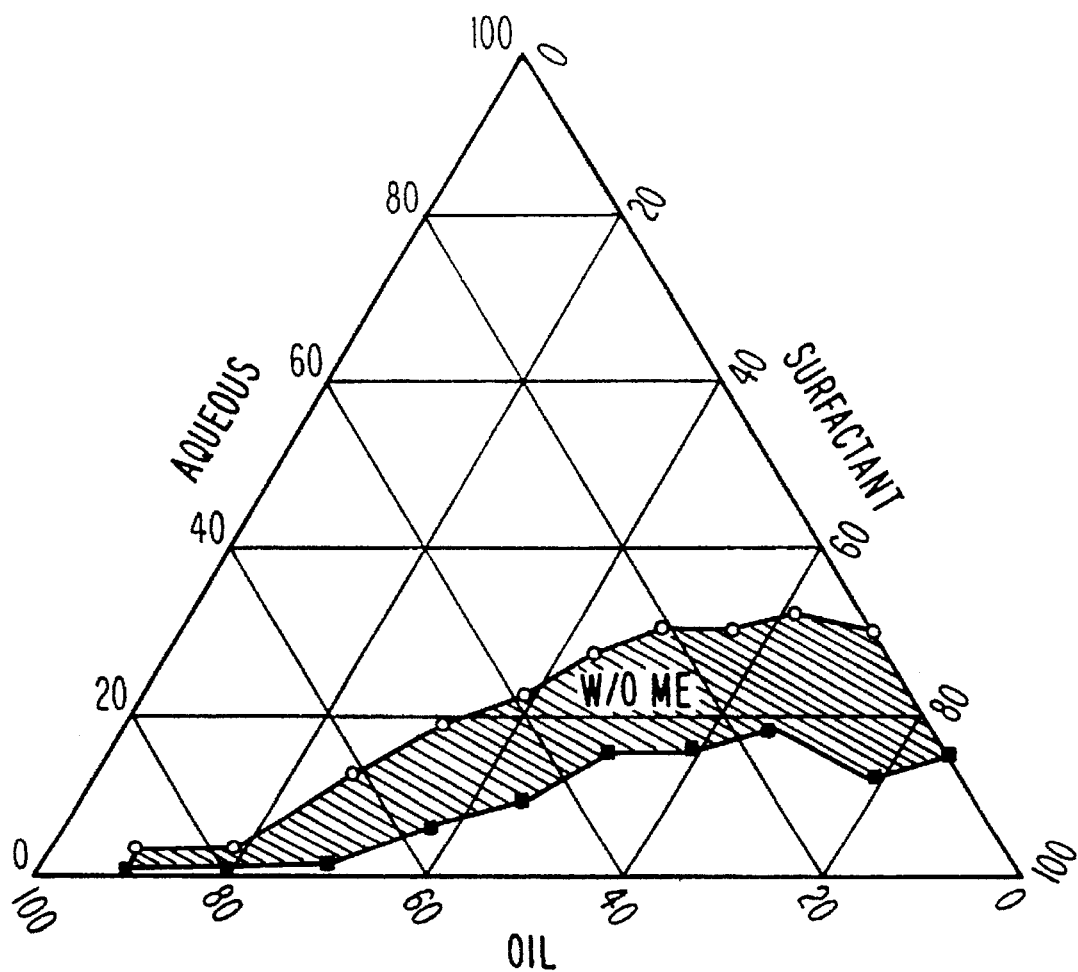
FIG. 2 is a phase diagram of an embodiment of the present invention depicting the water-in-oil microemulsion region wherein the oil is Captex 200, the aqueous phase is 0.9% wt. NaCl aqueous solution, and the surfactant mixture is Capmul MCM:Centrophase 31:Tween 80.

In FIG. 2 the oil is Captex 200, the aqueous phase is 0.9% wt. NaCl aqueous solution, and the surfactant mixture is Capmul MCM:Centrophase 31:Tween 80 in a weight ratio of 46:10.6:43.4.

Figure 3:
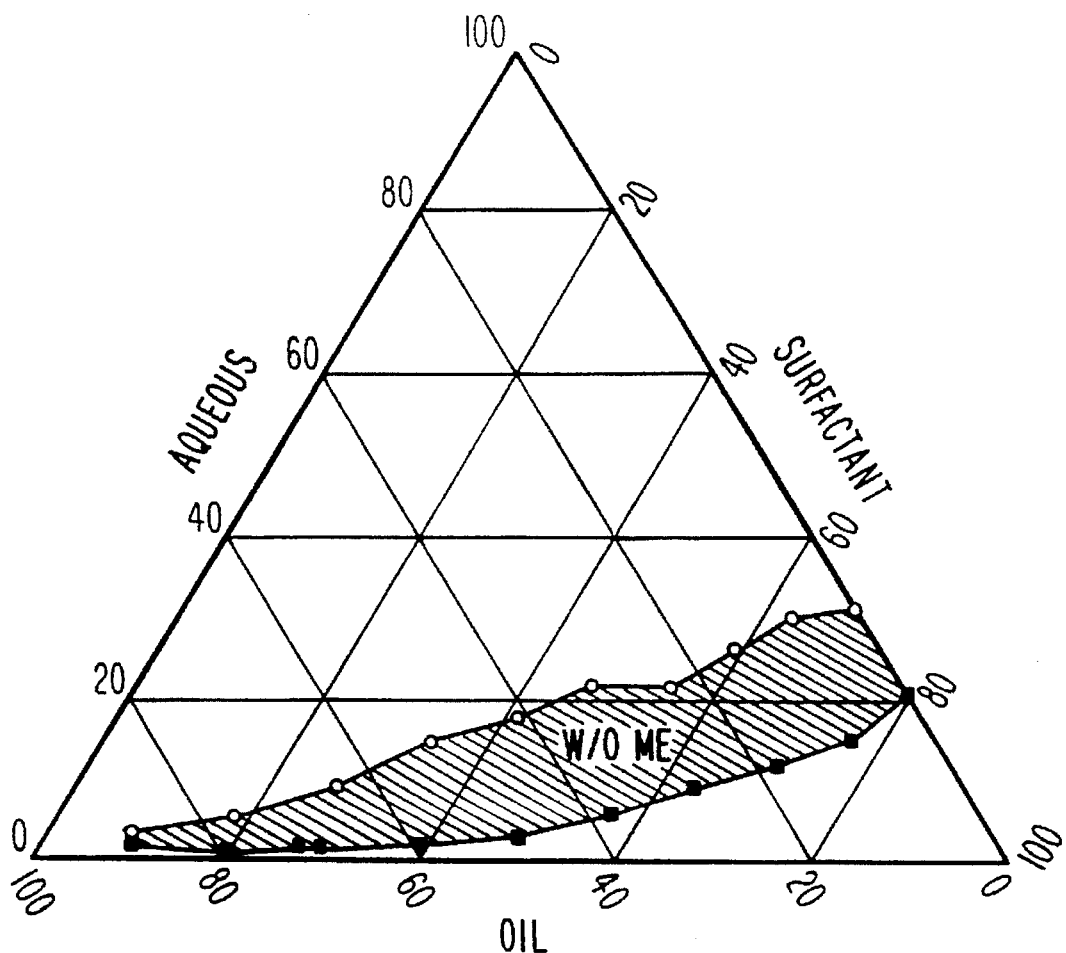
FIG. 3 is a phase diagram of an embodiment of the present invention depicting the water-in-oil microemulsion region wherein the oil is Captex 200, the aqueous phase is 0.9% wt. NaCl aqueous solution, and the surfactant mixture is Capmul MCM:Centrophase 31:Cremophor EL.

In FIG. 3 the oil is Captex 200, the aqueous phase is 0.9% wt. NaCl aqueous solution, and the surfactant mixture is Capmul MCM:Centrophase 31:Cremophor EL in a weight ratio of 31.5:6:62.5. This system includes the ME-1 used in Example 18.

Figure 4:
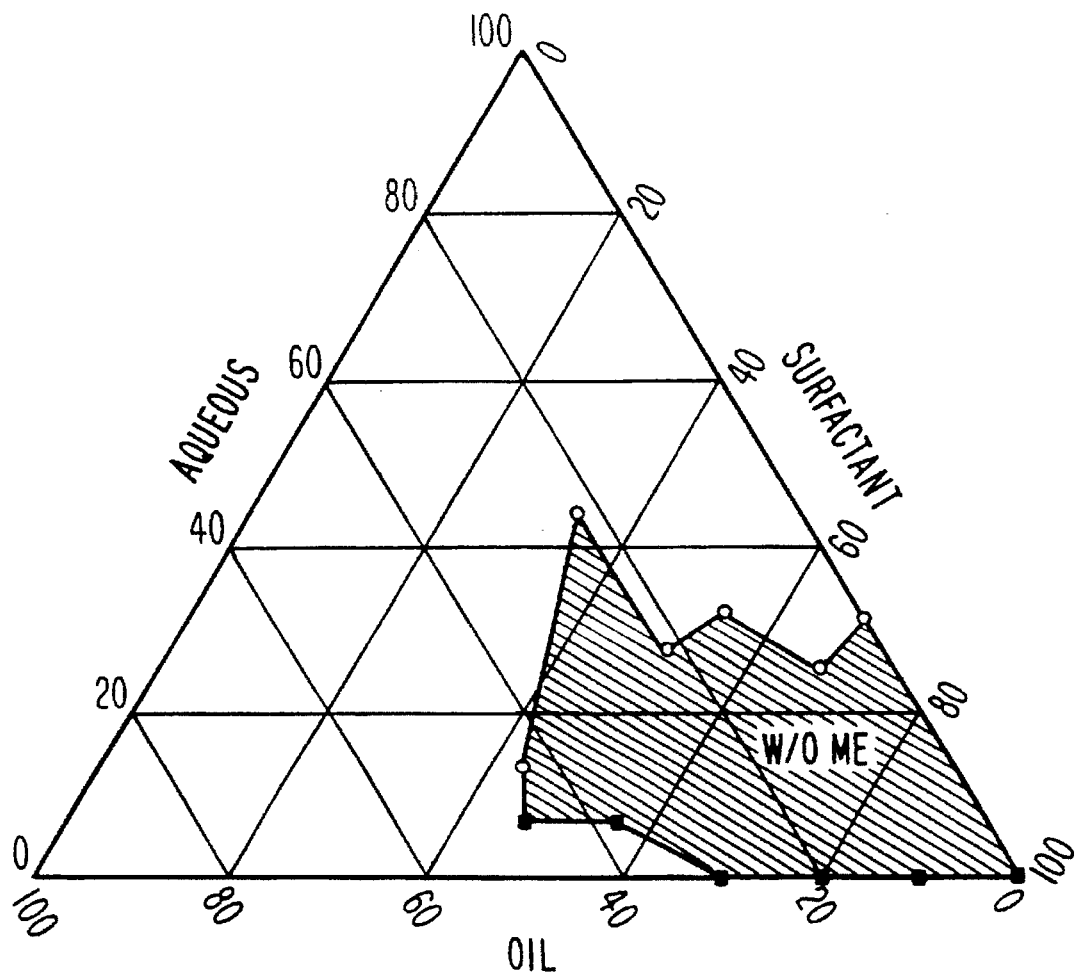
FIG. 4 is a phase diagram of an embodiment of the present invention depicting the water-in-oil microemulsion region wherein the oil is Whitepsol H-15, the aqueous phase is a 20% wt. Sorbitol in 0.9% wt. NaCl aqueous solution, and the surfactant mixture is Capmul MCM:Myverol 18–92:Tween 80.

In FIG. 4 the oil is Whitepsol H-15, the aqueous phase is a 20% wt. Sorbitol in 0.9% wt. NaCl aqueous solution, and the surfactant mixture is Capmul MCM:Myverol 18–92:Tween 80 in a weight ratio of 15.4:8.5:76.

Figure 5:
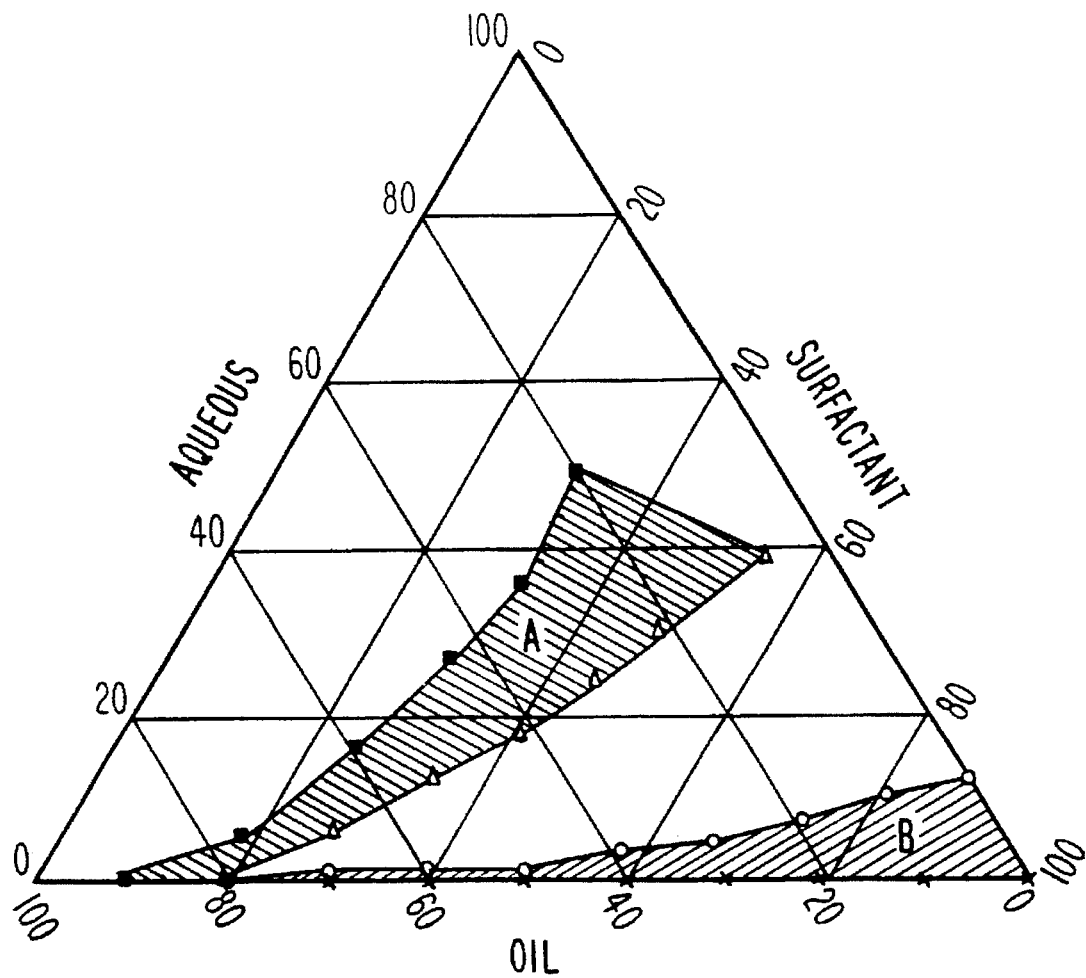
FIG. 5 is a phase diagram of an embodiment of the present invention depicting the water-in-oil microemulsion region wherein the oil is MYVACET 9–45K, the aqueous phase is 0.9% wt. NaCl aqueous solution, and the surfactant mixture is Capmul MCM:Myverol 18–92:Cremophor EL.

In FIG. 5 the oil is MYVACET 9–45K, the aqueous phase is 0.9% wt. NaCl aqueous solution, and the surfactant mixture is Capmul MCM:Myverol 18–92:Cremophor EL in a weight ratio of 45.5:5.2:49.2.

EXAMPLE 26

Water-in-oil microemulsions depicted in FIGS. 1–5 can be made using both about 25 mg peptide/ml and 75 mg peptide/ml aqueous phase using both peptides cyclo(S,S)-N$^\alpha$-acetyl-Cys-(N$^\alpha$-methyl)Arg-Gly-Asp-Pen-NH$_2$) (SEQ ID NO:1) and His-D-Trp-Ala-Trp-D-Phe-Lys-NH$_2$).

What is claimed is:

1. A biologically compatible water-in-oil microemulsion composition that converts to an oil-in-water emulsion by the addition of water, comprising:
   (a) up to about 60 volume percent of an internal dispersed aqueous phase comprising an effective amount of a biologically active material that is water soluble;
   (b) from about 5 to 99 volume percent of a continuous oil phase comprising at least one pharmaceutically-acceptable oil comprising a $C_{9-83}$ triglyceride, a $C_{7-55}$ diester of propylene glycol, or mixtures thereof; and
   (c) from about 1 to about 70 volume percent of a surfactant or surfactant mixture comprising a $C_8$ fatty acid salt, wherein the surfactant or surfactant mixture has an HLB value of at least 7.

2. The water-in-oil microemulsion composition of claim 1 wherein the biologically active material is a therapeutic and is a protein, peptide, immunogen, or other pharmaceutically active material and the water:oil partition coefficient of the active material is greater than 10:1.

3. The water-in-oil microemulsion composition of claim 2 wherein the biologically active material is a protein or a peptide.

4. The water-in-oil microemulsion composition of claim 3 wherein the composition is a liquid.

5. The water-in-oil microemulsion composition of claim 4 wherein the oil phase comprises a $C_{20-60}$ triglyceride, a $C_{15-40}$ diester of propylene glycol, or mixtures thereof.

6. The water-in-oil microemulsion composition of claim 4 wherein the surfactant mixture further comprises a $C_8$ fatty acid.

7. The water-in-oil microemulsion composition of claim 4 wherein the surfactant mixture further comprises a $C_{9-13}$ monoglyceride.

8. The water-in-oil microemulsion composition of claim 4 further comprising a modifier in an amount effective to convert the water-in-oil microemulsion to an oil-in-water microemulsion upon addition of aqueous fluid.

9. The water-in-oil microemulsion composition of claim 3 wherein the composition is a solid at about 23° C.

10. A biologically compatible water-in-oil microemulsion composition that converts to an oil-in-water emulsion by the addition of water, comprising:
   (a) up to about 20 volume percent of an internal dispersed aqueous phase comprising an effective amount of a biologically active material that is water soluble;
   (b) from about 30 to 99 volume percent of a continuous oil phase comprising at least one pharmaceutically-acceptable oil comprising a $C_{9-83}$ triglyceride, a $C_{7-55}$ diester of propylene glycol, or mixtures thereof; and
   (c) from about 1 to about 70 volume percent of a surfactant or surfactant mixture comprising a $C_8$ fatty acid salt, wherein the surfactant or surfactant mixture has an HLB value of from 7 to 14.

11. The water-in-oil microemulsion composition of claim 10 wherein the biologically active material is a therapeutic and is a protein, peptide, immunogen, or other pharmaceutically active material.

12. The water-in-oil microemulsion composition of claim 10 wherein the biologically active material is a protein or a peptide.

13. The water-in-oil microemulsion composition of claim 12 wherein the composition is a liquid.

14. The water-in-oil microemulsion composition of claim 13 wherein the oil phase comprises a $C_{20-60}$ triglyceride, a $C_{15-40}$ diester of propylene glycol, or mixtures thereof.

15. The water-in-oil microemulsion composition of claim 13 wherein the surfactant mixture further comprises a $C_8$ fatty acid.

16. The water-in-oil microemulsion composition of claim 13 wherein the surfactant mixture further comprises a mixture of mono- and di-glycerides of capric and caprylic acid.

17. The water-in-oil microemulsion composition of claim 13 wherein the composition is a solid at about 23° C.

18. A method of administering a biologically active material to an animal, comprising:
   (a) providing a biologically compatible water-in-oil microemulsion composition that converts to an oil-in-water emulsion by the addition of water, comprising:
      (1) up to about 20 volume percent of an internal dispersed aqueous phase comprising an effective amount of a therapeutic, biologically active material that is water soluble;
      (2) from about 30 to 99 volume percent of a continuous oil phase comprising at least one pharmaceutically-acceptable oil comprising a $C_{9-83}$ triglyceride, a $C_{7-55}$ diester of propylene glycol, or mixtures thereof; and
      (3) from about 1 to about 70 volume percent of a surfactant or surfactant mixture comprising a $C_8$ fatty acid salt, wherein the surfactant or surfactant mixture has an HLB value of from 7 to 14;
   (b) administering said composition to an animal.

19. The method of claim 18 wherein said biologically active material is a protein or peptide.

20. The method of claim 19 wherein said water-in-oil microemulsion is a liquid and wherein said administration is oral.

* * * * *